(12) United States Patent
Fuchss

(10) Patent No.: US 7,781,453 B2
(45) Date of Patent: Aug. 24, 2010

(54) AMINOPYRIDINE-DERIVATIVES

(75) Inventor: Thomas Fuchss, Radolfzell (DE)

(73) Assignee: Altana Pharma AG, Constance (DE)

(*) Notice: Subject to any disclaimer, the term of this patent is extended or adjusted under 35 U.S.C. 154(b) by 245 days.

(21) Appl. No.: 11/984,364

(22) Filed: Nov. 16, 2007

(65) Prior Publication Data
US 2008/0176894 A1 Jul. 24, 2008

Related U.S. Application Data

(63) Continuation of application No. 10/573,204, filed as application No. PCT/EP2004/052373 on Sep. 30, 2004, now Pat. No. 7,317,021.

(30) Foreign Application Priority Data
Oct. 1, 2003 (EP) .................................. 03022040

(51) Int. Cl.
A61K 31/437 (2006.01)
(52) U.S. Cl. ..................................... 514/303
(58) Field of Classification Search .................. 514/303
See application file for complete search history.

(56) References Cited

U.S. PATENT DOCUMENTS

| 4,045,564 | A | 8/1977 | Berntsson et al. |
| 7,138,399 | B2 | 11/2006 | Ulrich |

FOREIGN PATENT DOCUMENTS

| DE | 25 04 252 C2 | 8/1975 |
| EP | 0 125 756 A2 | 11/1984 |
| WO | 97/25030 A1 | 7/1997 |
| WO | 00/49015 A1 | 8/2000 |
| WO | 03/080607 A1 | 10/2003 |
| WO | 2005/030768 A1 | 4/2005 |
| WO | 2005/030769 A1 | 4/2005 |
| WO | 2005/030770 A1 | 4/2005 |
| WO | 2005/030771 A1 | 4/2005 |

OTHER PUBLICATIONS

McCann et al., Experimental gerontology, vol. 33, 1998, pp. 813-826.*
Kim et al., Biochemical Pharmacology, vol. 61, (2001), pp. 903-910.*
Hua, et al., Journal of Neuroimmunology, "Role of mitogen-activated protein kinases in inducible nitric oxide synthase and TNF expression in human fetal astrocytes", 2002, vol. 126, pp. 180-189.
Kim, et al., Neuroscience Letters, "Water-soluble chitosan inhibits the production of pro-inflammatory cytokine in human astrocytoma cells activated by amyloid B peptide and interleukin-1B", 2002, vol. 321, pp. 105-109.
D'Agostino, et al., European Journal of Pharmacology, "Tetracycline inhibits the nitric oxide synthase activity induced by endotoxin in cultured murine macrophages", 1998, vol. 346, pp. 283-290.

Kiss, et al., European Journal of Pharmacology, "Time-dependent actions of nitric oxide synthase inhibition on colonic inflammation induced by trinitrobenzene sulphonic acid in rats", 1997, vol. 336, pp. 219-224.
Sautebin, Fitoterapia, "Prostaglandins and nitric oxide as molecular targets for anti-inflammatory therapy", 2000, vol. 71, pp. S48-S57.
Ohtsuka, et al., The Journal of Pharmacology and Experimental Therapeutics, : PPA250[3-(2,4-Difluorophenyl)-6-{2-[4-(1H-imidazol-1-ylmethyl)Phenoxy]ethoxy}-2-phenylpyridine], a Novel Orally Effective Inhibitor of the Dimerization of Inducible Nitric-Oxide Synthase, Exhibits an Anti-Inflammatory Effect in Animal Models of Chronic Arthritis, 2002, vol. 303, No. 1, pp. 52-57.
Hansel, et al., Faseb J, "A selective inhibitor of inducible nitric oxide synthase inhibits exhaled breath nitric oxide in healthy volunteers and asthmatics", 2003, vol. 17, pp. 1298-1300.
Tinker, et al., J. Med. Chem., "1,2-Dihydro-4-quinazolinamines: Potent, Highly Selective Inhibitors of Inducible Nitric Oxide Synthase Which Show Antiinflammatory Activity in Vivo", 2003, vol. 26, pp. 913-916.
Kankuri, et al., The Journal of Pharmacology and Experimental Therapeutics, "Suppression of Acute Experimental Colitis by a Highly Selective Inducible Nitric-Oxide Synthase Inhibitor, N-[3-(Aminomethyl)benzyl]acetamidine", 2001, vol. 298, No. 3, pp. 1128-1132.
Liu, et al., Acta Pharmacol Sin, "Specificity of inducible nitric-oxide synthase inhibitors: prospects for their clinical therapy", 1999, vol. 20, No. 11, pp. 1052-1056.
Salvemini, et al., J. Clin. Invest., "Dual Inhibition of Nitric Oxide and Prostaglandin Production Contributes to the Antiinflammatory Properties of Nitric Oxide Synthase Inhibitors", 1995, vol. 96, pp. 301-308.
Cuzzocrea, et al., European Journal of Pharmacology, "Beneficial effects of GW274150, a novel, potent and selective inhibitor of INOA activity, in a rodent model of collagen-induced arthritis", 2002, vol. 453, pp. 119-129.

(Continued)

Primary Examiner—D. Margaret Seaman
Assistant Examiner—Niloofar Rahmani
(74) Attorney, Agent, or Firm—The Nath Law Group; Joshua B. Goldberg; Sheldon M. McGee

(57) ABSTRACT

The compounds of Formula (I)

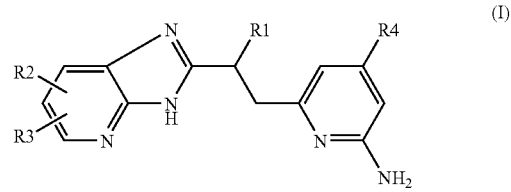

in which R1, R2, R3 and R4 have the meanings as given in the description are novel effective iNOS inhibitors.

10 Claims, No Drawings

OTHER PUBLICATIONS

Anazawa, T., et al., "Effect of Exposure to Cigarette Smoke on Carotid Artery Intimal Thickening: The Role of Inducible NO Synthase", Arterioscler Thromb Vasc Biol., vol. 24, pp. 1652-1658, (2004). American Heart Association, Inc.

Brindicci, C., et al., "Effects of Aminoguanidine, an Inhibitor of Inducible Nitric Oxide Synthase, on Nitric Oxide Production and Its Metabolites in Healthy Control Subjects, Healthy Smokers, and COPD Patients", Chest, vol. 135, pp. 353-367, (2009). American College of Chest Physicians.

Agusti, A.G.N., et al., "Serial measurements of exhaled nitric oxide during exacerbations of chronic obstructive pulmonary disease", Eur Respir J, vol. 14, pp. 523-528, (1999).

Kharitonov, S.A., et al., "Increased nitric oxide in exhaled air of asthmatic patients", Lancet, vol. 343, pp. 133-135, (1994).

Landgraf, R.G., et al., "Acute inhibition of inducible nitric oxide synthase but not its absence suppresses asthma-like responses", European Journal of Pharmacology, vol. 518, pp. 212-220, (2005). Elsevier B.V.

Lane, C. et al., "Epithelial inducible nitric oxide synthase activity is the major determinant of nitric oxide concentration in exhaled breath", Thorax, vol. 59, pp. 757-760, (2004).

Maziak, W., et al., "Exhaled Nitric Oxide in Chronic Obstructive Pulmonary Disease", Am J Respir Crit Care Med, vol. 157, pp. 998-1002, (1998).

Osoata, G.O., et al., "Peroxynitrite Elevation in Exhaled Breath Condensate of COPD and Its Inhibition by Fudosteine", Chest, pp. 1513-1520, (2009). American College of Chest Physicians.

Smith, A.D., et al., "Use of Exhaled Nitric Oxide Measurements to Guide Treatment in Chronic Asthma", N Engl J Med, vol. 352, pp. 2163-2173, (2005). Massachusetts Medical Society.

Connor, J.R., et al., "Suppression of adjuvant-induced arthritis by selective inhibition of inducible nitric oxide synthase", European Journal of Pharmacology, vol. 273, pp. 15-24, (1995). Elsevier Science B.V.

Pelletier, J-P., et al., "Reduced Progression of Experimental Osteoarthritis in Vivo by Selective Inhibition of Inducible Nitric Oxide Synthase", Arthritis & Rheumatism, vol. 41, No. 7, pp. 1275-1286, (1998).

* cited by examiner

AMINOPYRIDINE-DERIVATIVES

This application is a continuation application of U.S. Ser. No. 10/573,204, filed Mar. 24, 2006 now U.S. Pat. No. 7,317,021, which was filed under 35 U.S.C. 371 as a national stage of PCT/EP2004/052373, filed Sep. 30, 2004.

FIELD OF APPLICATION OF THE INVENTION

The invention relates to novel aminopyridine derivatives, which are used in the pharmaceutical industry for the production of pharmaceutical compositions.

KNOWN TECHNICAL BACKGROUND

In the German Patent Application DE 2504252 and in the European Patent Application EP 0125756 3H-imidazo[4,5-b]pyridine derivatives with anti-ulcer activity are described.

The International Application WO 0049015 describes pyridine compounds with inhibitory activity on the production of nitric oxide.

DESCRIPTION OF THE INVENTION

It has now been found that the aminopyridine derivatives, which are described in greater details below, have unanticipated, originative and sophisticated structural features and surprising and particularly advantageous properties.

The invention thus relates in a first embodiment (embodiment a) to compounds of formula I

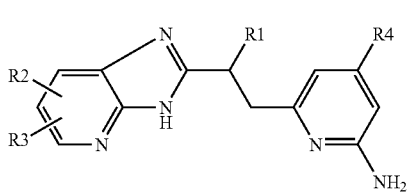

in which
R1 is hydrogen or 1-4C-alkyl,
R2 is hydrogen, halogen, hydroxyl, nitro, amino, 1-7C-alkyl, trifluoromethyl, 3-7C-cycloalkyl, 3-7C-cycloalkyl-1-4C-alkyl, 1-4C-alkoxy, completely or predominantly fluorine-substituted 1-4C-alkoxy, 1-4C-alkoxy-1-4C-alkyl, 1-4C-alkoxy-1-4C-alkoxy, 1-4C-alkoxycarbonyl, mono- or di-1-4C-alkylaminocarbonyl, mono- or di-1-4C-alkylaminosulfonyl, 1-4C-alkylcarbonylamino, 1-4C-alkylsulfonylamino, phenyl, R21- and/or R211-substituted phenyl, phenyl-1-4C-alkyl, phenyl-1-4C-alkyl wherein the phenyl moiety is substituted by R22, phenyl-1-4C-alkoxy, pyridyl, pyridyl substituted by R23, pyridyl-1-4C-alkyl, pyridyl-1-4C-alkyl wherein the pyridyl moiety is substituted by R24, in which
R21 is cyano, halogen, carboxyl, 1-4C-alkyl, 1-4C-alkoxy, aminocarbonyl, mono- or di-1-4C-alkylaminocarbonyl, 1-4C-alkylcarbonylamino, 1-4C-alkoxycarbonyl, aminosulfonyl, mono- or di-1-4C-alkylaminosulfonyl, amino, mono- or di-1-4C-alkylamino, trifluoromethyl, hydroxyl, phenylsulfonylamino, phenyl-1-4C-alkoxy, or —S(O)$_2$-Het, in which
Het is bonded to the adjacent sulfonyl group via a ring nitrogen atom, and is a 3- to 7-membered fully saturated heterocyclic ring comprising one nitrogen atom, to which the sulfonyl group is attached, and optionally one further heteroatom selected from N(R210), oxygen and sulfur, in which
R210 is 1-4C-alkyl,
R211 is halogen or 1-4C-alkoxy,
R22 is halogen, 1-4C-alkyl or 1-4C-alkoxy,
R23 is halogen, 1-4C-alkyl or 1-4C-alkoxy,
R24 is halogen, 1-4C-alkyl or 1-4C-alkoxy,
R3 is hydrogen, halogen, 1-4C-alkyl or 1-4C-alkoxy,
R4 is 1-4C-alkyl, or 1-4C-alkoxy, and the salts, the N-oxides and the salts of the N-oxides of these compounds.

1-4C-Alkyl is a straight-chain or branched alkyl radical having 1 to 4 carbon atoms. Examples are the butyl, isobutyl, sec-butyl, tert-butyl, propyl, isopropyl, and, particularly, the ethyl and methyl radicals.

1-7C-Alkyl is a straight-chain or branched alkyl radical having 1 to 7 carbon atoms. Examples are the heptyl, isoheptyl (5-methylhexyl), hexyl, isohexyl (4-methylpentyl), neohexyl (3,3-dimethylbutyl), pentyl, isopentyl (3-methylbutyl), neopentyl (2,2-dimethylpropyl), butyl, isobutyl, sec-butyl, tert-butyl, propyl, isopropyl, ethyl and methyl radicals.

1-4C-Alkoxy is a radical which, in addition to the oxygen atom, contains a straight-chain or branched alkyl radical having 1 to 4 carbon atoms. Alkoxy radicals having 1 to 4 carbon atoms which may be mentioned in this context are, for example, the butoxy, isobutoxy, sec-butoxy, tert-butoxy, propoxy, isopropoxy, and, particularly, the ethoxy and methoxy radicals.

3-7C-Cycloalkyl stands for cyclopropyl, cyclobutyl, cyclopentyl, cyclohexyl and cycloheptyl, of which cyclopropyl, cyclobutyl and cyclopentyl are preferred.

3-7C-Cycloalkyl-1-4C-alkyl stands for one of the abovementioned 1-4C-alkyl radicals, which is substituted by one of the abovementioned 3-7C-cycloalkyl radicals. 3-7C-Cycloalkyl-1-2C-alkyl, particularly 3-7C-cycloalkylmethyl, radicals are to be emphasized in this connection. Examples which may be mentioned are the cyclopropylmethyl, the cyclohexylmethyl and the cyclohexylethyl radicals.

Halogen within the meaning of the present invention is iodine, bromine, chlorine or fluorine.

Completely or predominantly fluorine-substituted 1-4C-alkoxy is, for example, the 2,2,3,3,3-pentafluoropropoxy, the perfluoroethoxy, the 1,2,2-trifluoroethoxy and in particular the 1,1,2,2-tetrafluoroethoxy, the 2,2,2-trifluoroethoxy, the trifluoromethoxy and the difluoromethoxy radical, of which the difluoromethoxy radical is preferred. "Predominantly" in this connection means that more than half of the hydrogen atoms of the 1-4C-alkoxy groups are replaced by fluorine atoms.

1-4C-Alkoxy-1-4C-alkoxy stands for one of the abovementioned 1-4C-alkoxy radicals which is substituted by the same or another of the abovementioned 1-4C-alkoxy radicals. Examples which may be mentioned are the 2-(methoxy)ethoxy (—O—CH$_2$—CH$_2$—O—CH$_3$) and the 2-(ethoxy)ethoxy radical (—O—CH$_2$—O—CH$_2$—CH$_3$).

1-4C-Alkoxy-1-4C-alkyl stands for one of the abovementioned 1-4C-alkyl radicals which is substituted by one of the abovementioned 1-4C-alkoxy radicals. Examples which may be mentioned are the 2-ethoxyethyl and the 3-methoxypropyl radical.

Mono- or Di-1-4C-alkylamino radicals contain in addition to the nitrogen atom, one or two of the abovementioned 1-4C-alkyl radicals. Preferred are the di-1-4C-alkylamino radicals, especially the dimethylamino, the diethylamino and the diisopropylamino radicals.

Mono- or Di-1-4C-alkylaminocarbonyl radicals contain in addition to the carbonyl group one of the abovementioned mono- or di-1-4C-alkylamino radicals. Examples which may be mentioned are the N-methyl- the N,N-dimethyl-, N-ethyl-, the N-propyl-, the N,N-diethyl- and the N-isopropylaminocarbonyl radical.

Mono- or Di-1-4C-alkylaminosulfonyl stands for a sulfonyl group to which one of the abovementioned mono- or di-1-4C-alkylamino radicals is bonded. Examples which may be mentioned are the methylaminosulfonyl, the dimethylaminosulfonyl and the ethylaminosulfonyl radical.

An 1-4C-Alkylcarbonylamino radical is, for example, the propionylamino [$C_3H_7C(O)NH$—] and the acetylamino radical [$CH_3C(O)NH$—].

An 1-4C-Alkylsulfonylamino radical is, for example, the propylsulfonylamino [$C_3H_7S(O)_2NH$—] and the methylsulfonylamino radical [$CH_3S(O)_2NH$—].

1-4C-Alkoxycarbonyl is a carbonyl group to which one of the abovementioned 1-4C-alkoxy radicals is bonded. Examples are the methoxycarbonyl [$CH_3O$—$C(O)$—] and the ethoxycarbonyl [$CH_3CH_2O$—$C(O)$—] radicals.

Phenyl-1-4C-alkoxy stands for one of the abovementioned 1-4C-alkoxy radicals, which is substituted by the phenyl radical. Examples which may be mentioned are the benzyloxy and the phenethoxy radical.

Phenyl-1-4C-alkyl stands for one of the abovementioned 1-4C-alkyl radicals, which is substituted by a phenyl radical. Examples which may be mentioned are the phenethyl and the benzyl radical.

Pyridyl-1-4C-alkyl stands for one of the abovementioned 1-4C-alkyl radicals, which is substituted by a pyridyl radical. Examples which may be mentioned are the pyridylethyl and the pyridylmethyl radical.

Pyridyl includes pyridin-2-yl, pyridin-3-yl and pyridin-4-yl.

N-oxide denotes the N-oxide on the pyridine which is substituted by R4.

Het is bonded to the adjacent sulfonyl group via a ring nitrogen atom, and is a 3- to 7-membered fully saturated heterocyclic ring comprising one nitrogen atom, to which the sulfonyl group is attached, and optionally one further heteroatom selected from N(R210), oxygen and sulfur.

Examples of Het may include, without being restricted thereto, aziridin-1-yl, azetidin-1-yl, pyrrolidin-1-yl, piperidin-1-yl, homopiperidin-1-yl, morpholin-4-yl, thiomorpholin-4-yl, 4N-(1-4C-alkyl)-homopiperazin-1-yl, or 4N-(1-4C-alkyl)-piperazin-1-yl such as e.g. 4N-methyl-piperazin-1-yl.

Compounds according to this invention which may be mentioned include for example compounds of formula Ia

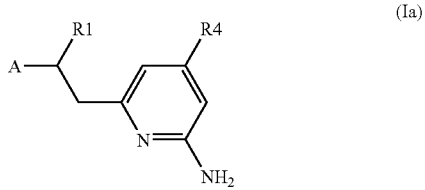

(Ia)

in which R1 and R4 have the meanings given above and A suitably includes 3H-imidazo[4,5-b]pyridin-2-yl, 7-methyl-3H-imidazo[4,5-b]pyridin-2-yl, 5,7-dimethyl-3H-imidazo[4,5-b]pyridin-2-yl, 5-methoxy-3H-imidazo[4,5-b]pyridin-2-yl, 6-brom-3H-imidazo[4,5-b]pyridin-2-yl, 7-methoxy-3H-imidazo[4,5-b]pyridin-2-yl, 7-hydroxy-3H-imidazo[4,5-b]pyridin-2-yl, 7-ethoxy-3H-imidazo[4,5-b]pyridin-2-yl, 7-(2-methoxy-ethoxy)-imidazo[4,5-b]pyridin-2-yl, 7-(1,1,1-trifluoroethoxy)-3H-imidazo[4,5-b]pyridin-2-yl, 7-(phenylethoxy)-3H-imidazo[4,5-b]pyridin-2-yl, 7-(phenylethyl)-3H-imidazo[4,5-b]pyridin-2-yl, 7-(tolylethyl)-3H-imidazo[4,5-b]pyridin-2-yl, 7-(pyrid-4-ylethyl)-3H-imidazo[4,5-b]pyridin-2-yl, 7-(pyrid-2-ylethyl)-3H-imidazo[4,5-b]pyridin-2-yl, 7-(pyrid-3-ylethyl)-3H-imidazo[4,5-b]pyridin-2-yl, 7-(4-methoxypyrid-2-ylethyl)-3H-imidazo[4,5-b]pyridin-2-yl, 6-phenyl-3H-imidazo[4,5-b]pyridin-2-yl, 6-n-butyl-3H-imidazo[4,5-b]pyridin-2-yl, 6-(4-methoxyphenyl)-3H-imidazo[4,5-b]pyridin-2-yl, 6-(4-methylphenyl)-3H-imidazo[4,5-b]pyridin-2-yl, 6-nitro-3H-imidazo[4,5-b]pyridin-2-yl, 6-(pyrid-3-yl)-3H-imidazo[4,5-b]pyridin-2-yl, 6-(4-cyanophenyl)-3H-imidazo[4,5-b]pyridin-2-yl, 6-methyl-3H-imidazo[4,5-b]pyridin-2-yl, 6-trifluoromethyl-3H-imidazo[4,5-b]pyridin-2-yl, 6-iodo-3H-imidazo[4,5-b]pyridin-2-yl, 6-(4-aminophenyl)-3H-imidazo[4,5-b]pyridin-2-yl, 6-(4-dimethylaminophenyl)-3H-imidazo[4,5-b]pyridin-2-yl, 6-(4-hydroxyphenyl)-3H-imidazo[4,5-b]pyridin-2-yl, 6-(4-trifluoromethylphenyl)-3H-imidazo[4,5-b]pyridin-2-yl, 6-(4-phenylsulfonylaminophenyl)-3H-imidazo[4,5-b]pyridin-2-yl, 6-(3,4-dimethoxyphenyl)-3H-imidazo[4,5-b]pyridin-2-yl, 6-(3,4-dichlorophenyl)-3H-imidazo[4,5-b]pyridin-2-yl, 6-(3,5-dichlorophenyl)-3H-imidazo[4,5-b]pyridin-2-yl, 6-(4-benzyloxyphenyl)-3H-imidazo[4,5-b]pyridin-2-yl, 6-(4-benzyloxy-3-fluoro-phenyl)-3H-imidazo[4,5-b]pyridin-2-yl, 6-(3-methyl-butyl)-3H-imidazo[4,5-b]pyridin-2-yl, 6-cyclohexylmethyl-3H-imidazo[4,5-b]pyridin-2-yl, 6-benzyl-3H-imidazo[4,5-b]pyridin-2-yl, 6-ethyl-3H-Imidazo[4,5-b]pyridin-2-yl, 6-isopropyl-3H-imidazo[4,5-b]pyridin-2-yl, 6-n-pentyl-3H-imidazo[4,5-b]pyridin-2-yl, 6-(4-chlorophenyl)-3H-imidazo[4,5-b]pyridin-2-yl, 6-(4-fluorophenyl)-3H-imidazo[4,5-b]pyridin-2-yl, 6-(2-fluorophenyl)-3H-imidazo[4,5-b]pyridin-2-yl, 6-(4-bromophenyl)-3H-imidazo[4,5-b]pyridin-2-yl, 6-(3-bromophenyl)-3H-imidazo[4,5-b]pyridin-2-yl, 6-(3-methylphenyl)-3H-imidazo[4,5-b]pyridin-2-yl, 6-phenethyl-3H-imidazo[4,5-b]pyridin-2-yl, 6-(3-phenylpropyl)-3H-imidazo[4,5-b]pyridin-2-yl, 6-(4-bromo-phenyl-methyl)-3H-imidazo[4,5-b]pyridin-2yl, 6-(4-acetamido-phenyl)-3H-imidazo[4,5-b]pyridin-2-yl, 6-(4-methoxycarbonyl-phenyl)-3H-imidazo[4,5-b]pyridin-2-yl, 6-(4-carboxy-phenyl)-3H-imidazo[4,5-b]pyridin-2-yl, 6-methoxycarbonyl-3H-imidazo[4,5-b]pyridin-2-yl, 6-(4-dimethylamino-carbonyl-phenyl)-3H-imidazo[4,5-b]pyridin-2-yl, 6-(4-dimethylaminosulphonyl-phenyl)-3H-imidazo[4,5-b]pyridin-2-yl, 6-(4-diethylaminosulphonyl-phenyl)-3H-imidazo[4,5-b]pyridin-2-yl, 6-(4-methylaminosulphonyl-phenyl)-3H-imidazo[4,5-b]pyridin-2-yl, 6-(4-aminosulphonyl-phenyl)-3H-imidazo[4,5-b]pyridin-2-yl, 6-(4-ethylaminosulphonyl-phenyl)-3H-imidazo[4,5-b]pyridin-2-yl or 6-(3-fluoro-4-dimethylaminosulphonyl-phenyl)-3H-imidazo[4,5-b]pyridin-2-yl, or 6-[4-(azetidine-1-sulfonyl)-phenyl]-3H-imidazo[4,5-b]pyridin-2-yl, 6-[4-(pyrrolidine-1-sulfonyl)-phenyl]-3H-imidazo[4,5-b]pyridin-2-yl, 6[4-(piperidine-1-sulfonyl)-phenyl]-3H-imidazo[4,5-b]pyridin-2-yl, 6-[4-(4-methyl-piperazine-1-sulfonyl)-phenyl]-3H-imidazo[4,5-b]pyridin-2-yl, 6-(3-hydroxyphenyl)-3H-imidazo[4,5-b]pyridin-2-yl, 6-(3,5-dichloro-phenyl)-3H-imidazo[4,5-b]pyridin-2-yl or 6-(4-benzyloxyphenyl)-3H-imidazo[4,5-b]pyridin-2-yl.

Compounds according to this invention which may be in particular mentioned include for example those compounds of formula Ia as shown above, in which R1 is hydrogen, R4 is methyl, and A has one of the meanings mentioned in the foregoing paragraph.

Suitable salts for compounds of formula I—depending on substitution—are all acid addition salts or all salts with bases. Particular mention may be made of the pharmacologically tolerable inorganic and organic acids and bases customarily used in pharmacy. Those suitable are, on the one hand, water-insoluble and, particularly, water-soluble acid addition salts with acids such as, for example, hydrochloric acid, hydrobromic acid, phosphoric acid, nitric acid, sulphuric acid, acetic acid, citric acid, D-gluconic acid, benzoic acid, 2-(4-hydroxybenzoyl)benzoic acid, butyric acid, sulphosalicylic acid, maleic acid, lauric acid, malic acid, fumaric acid, succinic acid, oxalic acid, tartaric acid, embonic acid, stearic acid, toluenesulphonic acid, methanesulphonic acid or 3-hydroxy-2-naphthoic acid, the acids being employed in salt preparation—depending on whether a mono- or polybasic acid is concerned and depending on which salt is desired—in an equimolar quantitative ratio or one differing therefrom.

On the other hand, salts with bases are—depending on substitution—also suitable. As examples of salts with bases are mentioned the lithium, sodium, potassium, calcium, aluminium, magnesium, titanium, ammonium, meglumine or guanidinium salts, here, too, the bases being employed in salt preparation in an equimolar quantitative ratio or one differing therefrom.

Pharmacologically intolerable salts, which can be obtained, for example, as process products during the preparation of the compounds according to the invention on an industrial scale, are converted into pharmacologically tolerable salts by processes known to the person skilled in the art.

According to expert's knowledge the compounds of the invention as well as their salts may contain, e.g. when isolated in crystalline form, varying amounts of solvents. Included within the scope of the invention are therefore all solvates and in particular all hydrates of the compounds of formula I as well as all solvates and in particular all hydrates of the salts of the compounds of formula I.

A person skilled in the art knows on the base of his/her expert knowledge that the compounds according to this invention can exist, with regard to the fused imidazo ring, in different tautomeric forms such as e.g. in the 1-H form or, preferably, in the 3-H form, which is shown in formula I. The invention includes all conceivable tautomers in pure form as well as in any mixing ratio. Particularly the present invention includes the pure 1-H- and, preferably, 3-H-tautomers as well as any mixtures thereof.

Compounds according to embodiment a of this invention worthy to be mentioned are those compounds of formula I in which R1 is hydrogen or 1-2C-alkyl,
R2 is hydrogen, halogen, phenyl, or R21- and/or R211-substituted phenyl, in which
R21 is 1-4C-alkyl, cyano, halogen, mono- or di-1-4C-alkylamino, trifluoromethyl, mono- or di-1-4C-alkylaminosulfonyl, hydroxyl, phenyl-1-4C-alkoxy, or —S(O)$_2$-Het, in which
Het is azetidin-1-yl, pyrrolidin-1-yl, piperidin-1-yl, or 4N-(R210)-piperazin-1-yl, in which
R210 is 1-4C-alkyl,
R211 is halogen,
R3 is hydrogen,
R4 is methyl, or methoxy, and the salts, the N-oxides and the salts of the N-oxides of these compounds.

Compounds according to embodiment a of this invention more worthy to be mentioned are those compounds of formula I in which R1 is hydrogen, methyl or ethyl,
R2 is hydrogen, iodine, bromine, phenyl, or R21- and/or R211-substituted phenyl, in which
R21 is methyl, cyano, chlorine, fluorine, dimethylamino, trifluoromethyl, dimethylaminosulfonyl, hydroxyl, benzyloxy, or —S(O)$_2$-Het, in which
Het is azetidin-1-yl, pyrrolidin-1-yl, piperidin-1-yl, or 4N-methyl-piperazin-1-yl, in which
R211 is chlorine,
R3 is hydrogen,
R4 is methyl, or methoxy, and the salts, the N-oxides and the salts of the N-oxides of these compounds.

Compounds according to embodiment a of this invention in particular worthy to be mentioned are those compounds of formula I in which R1 is hydrogen or methyl,
R2 is bonded in the 6-position of the 3H-imidazo[4,5-b] pyridine ring, and is hydrogen, iodine, bromine, phenyl, 3-hydroxyl-phenyl, 4-(R21)-phenyl, or 3,5-di-chloro-phenyl, in which
R21 is methyl, cyano, chlorine, fluorine, dimethylamino, trifluoromethyl, dimethylaminosulfonyl, benzyloxy, or —S(O)$_2$-Het, in which
Het is azetidin-1-yl, pyrrolidin-1-yl, piperidin-1-yl, or 4N-methyl-piperazin-1-yl, in which
R3 is hydrogen,
R4 is methyl, or methoxy, and the salts, the N-oxides and the salts of the N-oxides of these compounds.

The invention relates in a second embodiment (embodiment b) to compounds of formula I, in which R1 is hydrogen or 1-4C-alkyl,
R2 is hydrogen, halogen, hydroxyl, nitro, amino, 1-7C-alkyl, trifluoromethyl, 3-7C-cycloalkyl, 3-7C-cycloalkyl-1-4C-alkyl, 1-4C-alkoxy, completely or predominantly fluorine-substituted 1-4C-alkoxy, 1-4C-alkoxy-1-4C-alkyl, 1-4C-alkoxy-1-4C-alkoxy, 1-4C-alkoxycarbonyl, mono- or di-1-4C-alkylaminocarbonyl, mono- or di-1-4C-alkylaminosulfonyl, 1-4C-alkylcarbonylamino, 1-4C-alkylsulfonylamino, phenyl, R21- and/or R211-substituted phenyl, phenyl-1-4C-alkyl, phenyl-1-4C-alkyl wherein the phenyl moiety is substituted by R22, phenyl-1-4C-alkoxy, pyridyl, pyridyl substituted by R23, pyridyl-1-4C-alkyl, pyridyl-1-4C-alkyl wherein the pyridyl moiety is substituted by R24, in which
R21 is cyano, halogen, carboxyl, 1-4C-alkyl, 1-4C-alkoxy, aminocarbonyl, mono- or di-1-4C-alkylaminocarbonyl, 1-4C-alkylcarbonylamino, 1-4C-alkoxycarbonyl, aminosulfonyl, mono- or di-1-4C-alkylaminosulfonyl, amino, mono- or di-1-4C-alkylamino, trifluoromethyl, hydroxyl, phenylsulfonylamino or phenyl-1-4C-alkoxy,
R211 is halogen or 1-4C-alkoxy,
R22 is halogen, 1-4C-alkyl or 1-4C-alkoxy,
R23 is halogen, 1-4C-alkyl or 1-4C-alkoxy,
R24 is halogen, 1-4C-alkyl or 1-4C-alkoxy,
R3 is hydrogen, halogen, 1-4C-alkyl or 1-4C-alkoxy,
R4 is 1-4C-alkyl, and the salts, the N-oxides and the salts of the N-oxides of these compounds.

Compounds according to embodiment b of this invention worthy to be mentioned are those compounds of formula I in which R1 is hydrogen or 1-2C-alkyl, R2 is hydrogen, halogen, phenyl, or R21-substituted phenyl, in which
R21 is 1-4C-alkyl, cyano, halogen, mono- or di-1-4C-alkylamino or trifluoromethyl,
R3 is hydrogen,
R4 is methyl, and the salts, the N-oxides and the salts of the N-oxides of these compounds.

Compounds according to embodiment b of this invention more worthy to be mentioned are those compounds of formula I in which
R1 is hydrogen, methyl or ethyl,
R2 is hydrogen, iodine, bromine, phenyl, or R21-substituted phenyl, in which
R21 is methyl, cyano, chlorine, fluorine, dimethylamino or trifluoromethyl,
R3 is hydrogen,
R4 is methyl, and the salts, the N-oxides and the salts of the N-oxides of these compounds.

The invention relates in a third embodiment (embodiment c) to compounds of formula I, in which
R1 is hydrogen or 1-4C-alkyl;

and in which either
R2 is R21- and R211-substituted phenyl, in which
R21 is 1-4C-alkyl, cyano, halogen, mono- or di-1-4C-alkylamino, trifluoromethyl, mono- or di-1-4C-alkylaminosulfonyl, hydroxyl, phenyl-1-4C-alkoxy, or —S(O)$_2$-Het, in which
Het is azetidin-1-yl, pyrrolidin-1-yl, piperidin-1-yl, or 4N-(1-4C-alkyl)-piperazin-1-yl, and
R211 is halogen, or
R2 is R21-substituted phenyl, in which
R21 is mono- or di-1-4C-alkylaminosulfonyl, hydroxyl, phenyl-1-4C-alkoxy, or —S(O)$_2$-Het, in which
Het is azetidin-1-yl, pyrrolidin-1-yl, piperidin-1-yl, or 4N-(1-4C-alkyl)-piperazin-1-yl;

and in which
R3 is hydrogen,
R4 is 1-4C-alkyl, and the salts, the N-oxides and the salts of the N-oxides of these compounds.

Compounds according to embodiment c of this invention worthy to be mentioned are those compounds of formula I in which
R1 is hydrogen or 1-2C-alkyl;

and in which either
R2 is R21- and R211-substituted phenyl, in which
R21 is methyl, cyano, chlorine, fluorine, dimethylamino, trifluoromethyl, dimethylaminosulfonyl, hydroxyl, benzyloxy, or —S(O)$_2$-Het, in which
Het is azetidin-1-yl, pyrrolidin-1-yl, piperidin-1-yl, or 4N-methyl-piperazin-1-yl, and
R211 is chlorine, or
R2 is R21-substituted phenyl, in which
R21 is dimethylaminosulfonyl, hydroxyl, benzyloxy, or —S(O)$_2$-Het, in which
Het is azetidin-1-yl, pyrrolidin-1-yl, piperidin-1-yl, or 4N-methyl-piperazin-1-yl;

and in which
R3 is hydrogen,
R4 is methyl, and the salts, the N-oxides and the salts of the N-oxides of these compounds.

Compounds according to embodiment c of this invention more worthy to be mentioned are those compounds of formula I in which
R1 is hydrogen or methyl;

and in which
R2 is bonded in the 6-position of the 3H-imidazo[4,5-b]pyridine ring, and is either dichlorophenyl, such as e.g. 3,5-dichlorophenyl, or R21-substituted phenyl, in which
R21 is dimethylaminosulfonyl, hydroxyl, benzyloxy, or —S(O)$_2$-Het, in which
Het is azetidin-1-yl, pyrrolidin-1-yl, piperidin-1-yl, or 4N-methyl-piperazin-1-yl;

and in which
R3 is hydrogen,
R4 is methyl, and the salts, the N-oxides and the salts of the N-oxides of these compounds.

The invention relates in a fourth embodiment (embodiment d) to compounds of formula I, in which
R1 is hydrogen or methyl,
R2 is R21-substituted phenyl, in which
R21 is aminosulphonyl, mono- or di-1-4C-alkylaminosulfonyl, or —S(O)$_2$-Het, in which
Het is azetidin-1-yl, pyrrolidin-1-yl, piperidin-1-yl, or 4N-(1-4C-alkyl)-piperazin-1-yl,
R3 is hydrogen,
R4 is methyl, or methoxy, and the salts, the N-oxides and the salts of the N-oxides of these compounds.

Compounds according to embodiment d of this invention worthy to be mentioned are those compounds of formula I in which
R1 is hydrogen,
R2 is bonded in the 6-position of the 3H-imidazo[4,5-b]pyridine ring, and is 4-(R21)-phenyl, in which
R21 is aminosulphonyl, mono- or di-1-2C-alkylaminosulfonyl, or —S(O)$_2$-Het, in which
Het is azetidin-1-yl, pyrrolidin-1-yl, piperidin-1-yl, or 4N-(1-2C-alkyl)-piperazin-1-yl,
R3 is hydrogen,
R4 is methyl, or methoxy, and the salts, the N-oxides and the salts of the N-oxides of these compounds.

Compounds according to embodiment d of this invention more worthy to be mentioned are those compounds of formula Ia as shown above, in which
R1 is hydrogen,
R4 is methyl or methoxy, and
A is 6-(4-dimethylaminosulphonyl-phenyl)-3H-imidazo[4,5-b]pyridin-2-yl, 6-(4-diethylaminosulphonyl-phenyl)-3H-imidazo[4,5-b]pyridin-2-yl, 6-(4-methylaminosulphonyl-phenyl)-3H-imidazo[4,5-b]pyridin-2-yl, 6-(4-aminosulphonyl-phenyl)-3H-imidazo[4,5-b]pyridin-2-yl, 6-(4-ethylaminosulphonyl-phenyl)-3H-imidazo[4,5-b]pyridin-2-yl, 6-[4-(azetidine-1-sulfonyl)-phenyl]-3H-imidazo[4,5-b]pyridin-2-yl, 6-[4-(pyrrolidine-1-sulfonyl)- phenyl]-3H-imidazo[4,5-b]pyridin-2-yl, 6-[4-(piperidine-1-sulfonyl)-phenyl]-3H-imidazo[4,5-b]pyridin-2-yl, or 6-[4-(4-methyl-piperazine-1-sulfonyl)-phenyl]-3H-imidazo[4,5-b]pyridin-2-yl, and the salts, the N-oxides and the salts of the N-oxides of these compounds.

Compounds according to embodiment d of this invention in particular worthy to be mentioned are those compounds of formula Ia as shown above, in which
R1 is hydrogen,
R4 is methyl, and
A is 6-(4-dimethylaminosulphonyl-phenyl)-3H-imidazo[4,5-b]pyridin-2-yl, 6-(4-diethylaminosulphonyl-phenyl)-3H-imidazo[4,5-b]pyridin-2-yl, 6-(4-methylaminosulphonyl-phenyl)-3H-imidazo[4,5-b]pyridin-2-yl, 6-(4-aminosulphonyl-phenyl)-3H-imidazo[4,5-b]pyridin-2-yl, 6-(4-ethylaminosulphonyl-phenyl)-3H-imidazo[4,5-b]pyridin-2-yl, 6-[4-(azetidine-1-sulfonyl)-phenyl]-3H-imidazo[4,5-b]pyridin-2-yl, 6-[4-(pyrrolidine-1-sulfonyl)-phenyl]-3H-imidazo[4,5-b]pyridin-2-yl, 6-[4-(piperidine-1-sulfonyl)-phenyl]-3H-imidazo[4,5-]pyridin-2-yl, or 6-[4-(4-methyl-piperazine-1-sulfonyl)-phenyl]-3H-imidazo[4,5-b]pyridin-2-yl, and the salts, the N-oxides and the salts of the N-oxides of these compounds.

The compounds of formula I according to the invention are, depending on the meanings of R1, chiral compounds. The invention includes all conceivable enantiomers in pure form as well as in any mixing ratio including the racemate.

A special embodiment of the compounds of the present invention include those compounds of formula I in which R4 is methyl.

Another special embodiment of the compounds of the present invention include those compounds of formula I in which R4 is methoxy, and all the other substituents are as defined in any embodiment a to d, or as defined in any compound according to the present invention said to be mentioned above.

Another special embodiment of the compounds of the present invention include those compounds of formula I in which R3 is hydrogen.

Another special embodiment of the compounds of the present invention include those compounds of formula I in which R1 is ethyl or, particularly, methyl.

Another special embodiment of the compounds of the present invention include those compounds of formula I in which R1 is hydrogen.

Another special embodiment of the compounds of the present invention include those compounds of formula I in which R1 is hydrogen and R4 is methyl.

Another special embodiment of the compounds of the present invention include those compounds of formula I in which R1 is hydrogen and R4 is methoxy.

Another special embodiment of the compounds of the present invention include those compounds of formula I in which R4 is methyl and R3 is hydrogen.

Another special embodiment of the compounds of the present invention include those compounds of formula I in which R4 is methoxy and R3 is hydrogen.

Another special embodiment of the compounds of the present invention include those compounds of formula I in which R4 is methyl, R3 is hydrogen and R1 is ethyl, or in particular methyl, or in more particular hydrogen.

Another special embodiment of the compounds of the present invention include those compounds of formula I in which R4 is methoxy, R3 is hydrogen and R1 is ethyl, or in particular methyl, or in more particular hydrogen.

Another special embodiment of the compounds of the present invention include those compounds of formula I in which the substituent R2 is bonded to the 6-position of the imidazopyridine ring system.

The substituents R2 and R3 of compounds of formula I according to this invention can be attached at any possible ring carbon atoms of the pyridine portion of the 3H-imidazo[4,5-b]pyridine ring system, whereby a special embodiment of the compounds of the present invention include those compounds of formula I in which R2 is bonded to the 6-position of the imidazopyridine ring system and R3 is hydrogen.

Numbering of the imidazopyridine ring system:

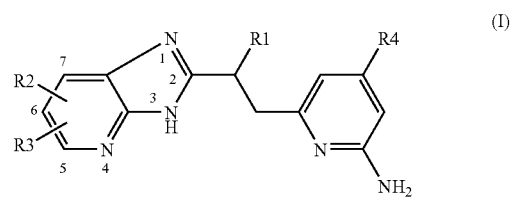

Another special embodiment of the compounds of the present invention include those compounds which comprise one or more of the following:
R1 is hydrogen,
R2 is bonded to the 6-position of the 3H-imidazo[4,5-b]pyridine ring,
R3 is hydrogen, and
R4 is methyl.

The substituents R21 and R211 of compounds according to this invention can be attached in the ortho, meta or para position with respect to the binding position in which the phenyl ring is bonded to the imidazopyridine ring system, whereby a special embodiment of the compounds of the present invention include those compounds of formula I in which the substituent R21 is attached in the meta or, particularly, para position, and whereby another special embodiment of the compounds of the present invention include those compounds of formula I in which R211 is hydrogen and the substituent R21 is attached in the para position.

The compounds of formula I according to the invention can, for example, be prepared according to those synthesis routes specified and shown below or in a manner described by way of example in the following examples or analogously or similarly thereto.

Reaction scheme 1 below shows by way of example the preparation of compounds of formula I, in which R1, R2, R3 and R4 have the meanings indicated above. In a first reaction step, diamino compounds of formula V, in which R2 and R3 have the meanings indicated above, are converted into 3H-imidazo[4,5-b]pyridine derivatives in a manner known from the literature or with analogous or similar use of processes known from the literature. For example, said compounds of formula V can be reacted with carboxylic acids or carboxylic acid derivatives of formula IV, in which R1 has the meanings indicated above, Y is a suitable leaving group, advantageously chlorine, and X is a cyano or carboxyl radical, to give in a condensation reaction compounds of formula III, in which R1, R2, R3 and Y have the meanings mentioned above. This condensation reaction can be carried out as known to one of ordinary skill in the art or as described by way of example in the following examples, for example, by using a suitable condensing agent such as preferably polyphosphoric acid in a suitable inert solvent or, preferably, without further solvent using an excess of condensing agent, preferably at elevated temperature, in particular at 130°-170° C.

Alternatively, compounds of the formula III can be also obtained by art-known procedures according to literature (e.g. as described in L. Bukowski et al., Pharmazie 1999, 54(9), 651-654 or G. Cleve et al., Liebigs Ann. Chem. 1971, 747, 158-171).

Compounds of formula III, in which R1, R2, R3 and Y have the meanings mentioned above, can be converted with certain phosphanes into corresponding phosphonium salts. Preferably, compounds of formula III are reacted with tributylphosphane or triphenylphosphane to give corresponding compounds of formula II, in which R1, R2, R3 and Y have the meanings mentioned above and R is butyl or phenyl. Said reaction can be carried out in a manner habitual per se or as described in the following examples in a suitable solvent such as, for example, acetonitrile or N,N-dimethylformamide or a mixture thereof, at elevated temperature, preferably at 90°-150° C., optionally in the presence of an auxiliary such as tetrabutylammonium iodide.

Reaction scheme 1:

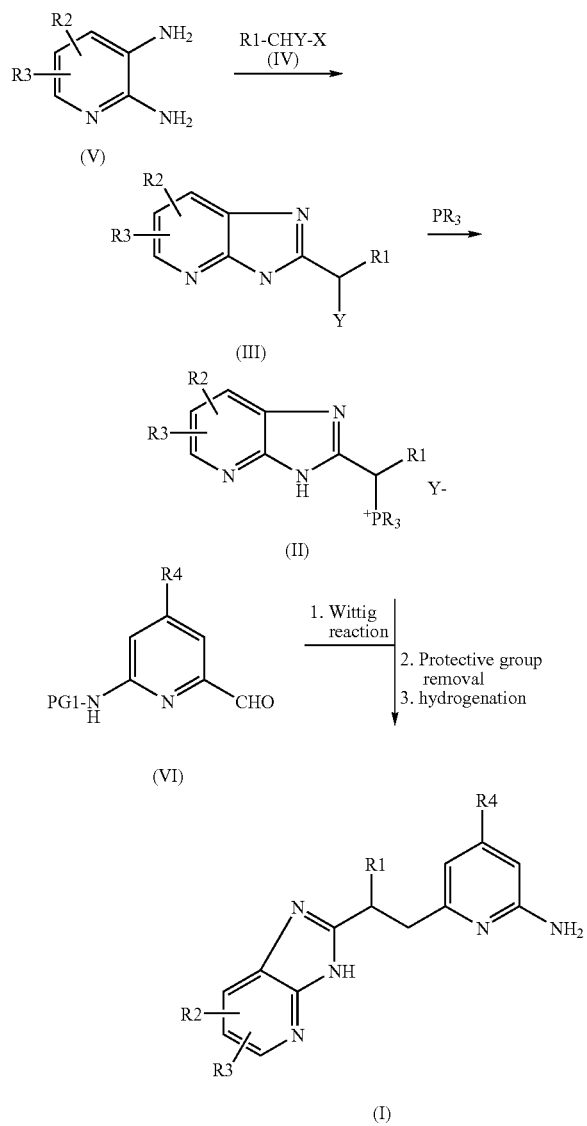

Compounds of formula II, in which R1, R2, R3 and Y have the meanings mentioned above and R is butyl or phenyl, are reacted with compounds of formula VI, in which R4 has the meanings given above and PG1 represents a suitable amino protective group, for example trityl, or acetyl (i.e. compounds of formula VIa), or one of those mentioned in "Protective Groups in Organic Synthesis" by T. Greene and P. Wuts (John Wiley & Sons, Inc. 1999, 3$^{rd}$ Ed.) or in "Protecting Groups (Thieme Foundations Organic Chemistry Series N Group" by P. Kocienski (Thieme Medical Publishers, 2000). Said reaction can be carried out in a manner as described in the following examples or as known to the person skilled in the art according to a Wittig reaction. In the scope of this invention, said Wittig reaction is preferably carried out in a suitable solvent such as, for example, methanol, tetrahydrofurane, toluene or a mixture thereof, using a suitable base such as, for example, sodium hydride or sodium methanolate, at room temperature or at elevated temperature, preferably at 20°-80° C. With regard to the configuration of the exocyclic double bond obtained by Wittig reaction, the outcome can be a Z- or E-configurated product or, in particular, a mixture thereof.

In the step following the Wittig reaction, the compound(s) obtained are converted into the corresponding free amino compound(s) by removal of the abovementioned protective group PG1 in a manner customary per se. For example, when PG1 is trityl, detritylation can be obtained, for example, with the aid of aqueous acetic acid according to the procedure specified in the following examples, or, when PG1 is acetyl, desacetylation can be obtained, for example, in aqueous sulphuric acid at elevated temperature, such as e.g. in 10% strength aqueous sulphuric acid at boiling temperature.

The reduction of the abovementioned exocyclic double bond following the deprotection reaction leads to desired compounds of formula I, in which R1, R2, R3 and R4 have the meanings given above. This reaction can be carried out as hydrogenation reaction according to procedures known to the person skilled in the art or according to the following examples in the presence of a suitable catalyst, such as, for example, palladium on active carbon or platinum dioxide, in a suitable solvent (e.g. in a lower alcohol, such as, for example, methanol). If necessary, acid, such as trifluoracetic acid or acetic acid, can be added to the solvent.

Compounds of formula IV are commercially available or can be obtained in a known manner.

Compounds of formula V are also commercially available or are known e.g. from S.—X. Cai et al., J. Med. Chem. 1997, 40(22), 3679-686 or from Cugola et al., Bioorg. Med. Chem. Lett. 1996, 22, 2749-2754 or can be prepared according to reaction scheme 2.

Reaction scheme 2:

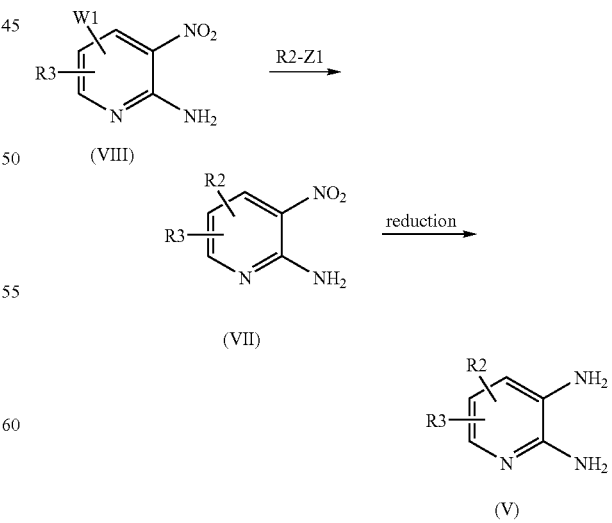

As shown in reaction scheme 2, in a first step compounds of formula VIII, in which R3 has the meanings mentioned above and W1 is a suitable leaving group (e.g. iodine or bromine), are reacted with boronic acids or boronic acid esters of formula R2-Z1, in which R2 is suitably phenyl or, in particular, R21- and/or R211-substituted phenyl and Z1 is a boronic acid group or a boronic acid ester group, under conditions appropriate for a Suzuki reaction to occur to give the corresponding compounds of formula VII.

Suitably, the Suzuki reaction is carried out as it is known to the person of ordinary skill in the art and/or in a manner as it is described below and specified by way of example in the following examples or analogously or similarly thereto.

The nitro group of compounds of formula VII is reduced in an art-known manner or as described in the following examples (e.g. with the aid of tin dichloride or by hydrogenation in the presence of a palladium catalyst) to give the corresponding diamino compounds of formula V.

Compounds of formula VIII are known (e.g. commercially available) or can be prepared according to known procedures or analogously or similarly thereto.

Compounds of formula R2-Z1 are also known (e.g. commercially available) or can be obtained in an art-known manner or analogously or similarly thereto.

Compounds of formula VI, in which R4 has the meanings mentioned above and PG1 represents said suitable protective group, can be obtained, for example, as described in the following examples or as outlined in reaction scheme 3.

In a first step the amino group of ester compounds of formula X, in which R4 has the meanings indicated above and the moiety —CO$_2$R' is preferably a methyl ester group, is protected by abovementioned suitable protective group PG1, preferably trityl, under standard conditions to afford corresponding compounds of formula IX.

Reaction scheme 3:

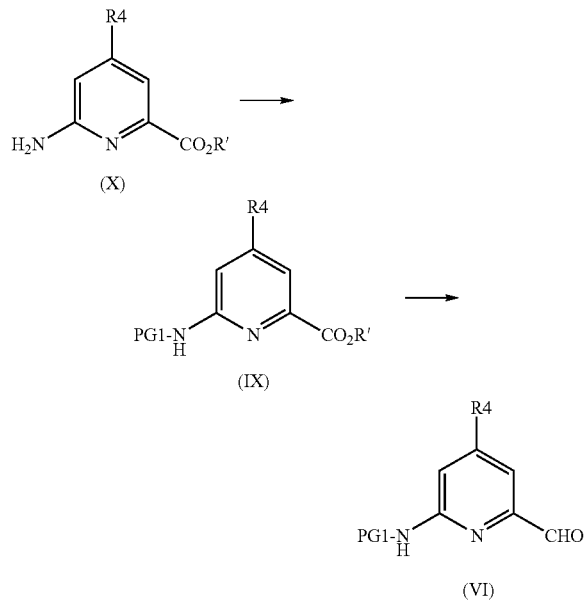

In a second step the ester group of compounds of formula IX, in which R4 has the meanings mentioned above and PG1 represents said suitable protective group, is reduced to give the desired compounds of formula VI. Said reduction reaction is carried out as described in the following examples or as known to the person skilled in the art using selective reducing agents such as, for example, suitable metal hydrids, particularly diisobutylaluminium hydride, in suitable solvents (e.g. toluene), optionally at reduced temperature.

Compounds of formula X, in which R4 has the meanings given above, are either known (see e.g. D. Markees et al. J. Am. Chem. Soc. 1956, 78, 4130-4133) or can be prepared as shown in the reaction scheme 4.

Reaction scheme 4 shows by way of example the synthesis of compounds of formula X, in which R4 is 1-4C-alkyl, particularly methyl, starting from corresponding compounds of formula XI, in which PG2 represents a suitable protective group, preferably acetyl. Thus in a first step, said compounds of formula XI are subjected to an oxidation reaction. This oxidation can be carried out in an art-known manner or as described in the following examples using a suitable oxidizing agent, such as, for example, potassium permangante. In a second step following oxidation the compounds obtained are converted into corresponding ester compounds—preferably the methyl ester compounds—of formula X. Said conversion can be carried out according to an art-known manner or as described in the following examples, e.g. using methanolic hydrochloric acid, preferably at boiling temperature, to obtain the methyl ester.

Reaction scheme 4:

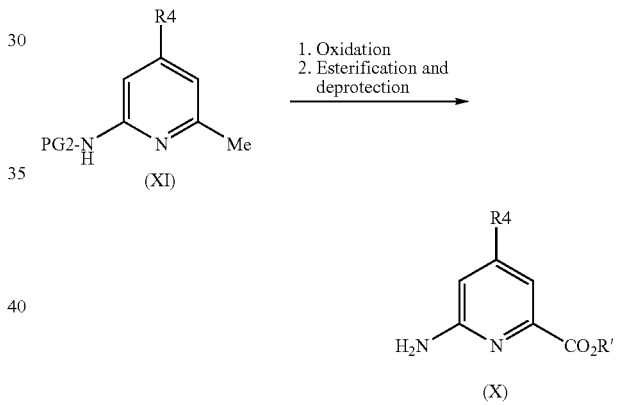

Compounds of formula XI are known (e.g. from M. Belcher, J. Am. Soc. 1952, 74, 1916-1918) or can be prepared analogously or similarly to known procedures.

Alternatively, compounds of formula VI, in which R4 is methyl and PG1 has the meanings given above, as well as compounds of formula VIa, in which R4 is methyl, can be also prepared according to the process outlined in reaction scheme 5.

Reaction scheme 5:

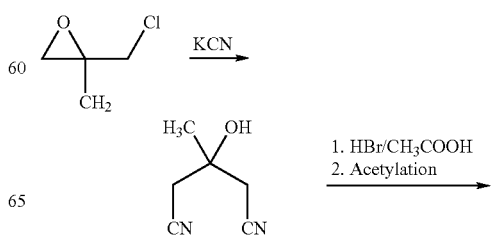

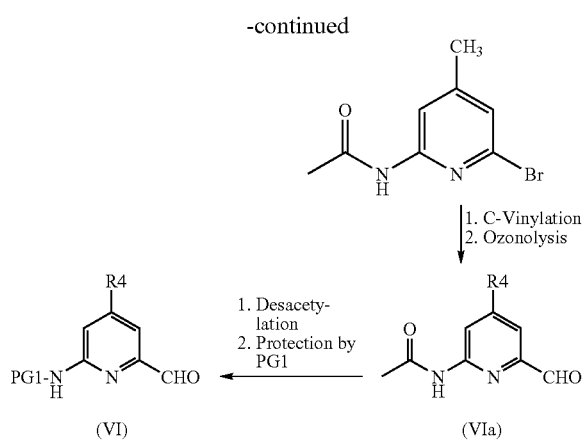

In an alternative, compounds of formula I, in which R1 is hydrogen and R2, R3 and R4 have the meanings given above, can be also obtained by the process shown in reaction scheme 6, described below and specified by way of example in the following examples.

Thus, carbonic acid compounds of formula V, in which R1 and R2 have the meanings given above, are amidified with diamino compounds of formulae XII or XIII, in which R4 and PG1 have the meanings mentioned above, in a manner customary per se to the skilled person using suitable amide bond linking reagents (e.g. O-[(ethoxycarbonyl)canomethylene-amino]—N,N,N',N'-tetramethyluronium tetrafluoroborate), the protective group PG1 is removed in an art-known manner and the amide is cyclized with the aid of an appropriate condensing agent (e.g. polyphosphoric acid) at elevated temperature. If the process started from compounds of formula XIII, the double bond is hydrogenated afterwards using standard procedures.

Accordingly, compounds of formula XII can be obtained from compounds of formula XIII by selective hydrogenation of the exocyclic double bond in a manner known to the skilled person (e.g. in the presence of palladium on carbon).

Compounds of formula XIII can be prepared starting from compounds of formula VI by lengthening of the exocyclic carbon chain, for example, by a Wittig reaction or, particularly, by a condensation reaction (with a malonic acid derivative, particularly with a malonic acid ester derivative) and subsequent saponification of the ester group. Said reactions can be carried out in a manner known to the skilled person or as described in the following examples or analogously or similarly thereto.

Reaction scheme 6:

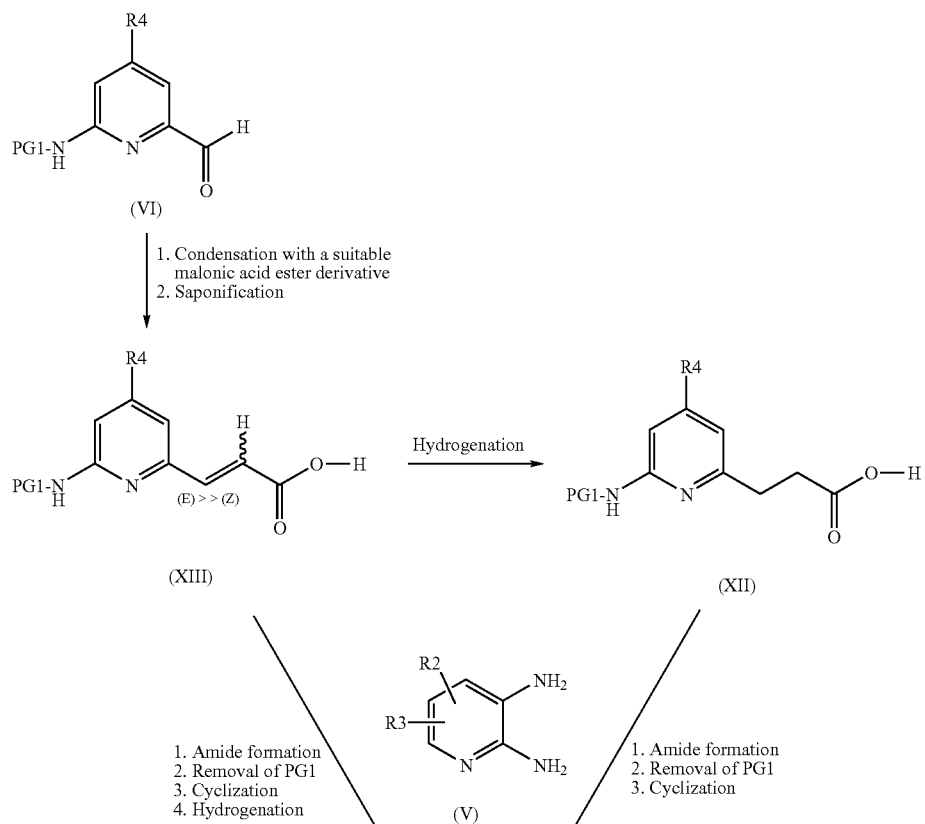

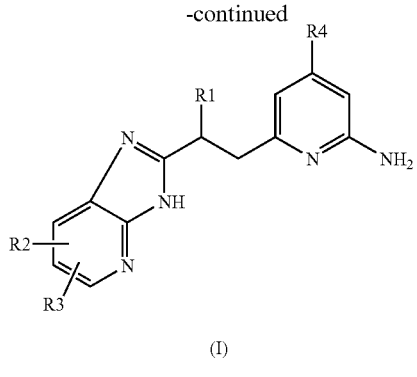

(I)

In a further alternative, compounds of formula I, in which R1, R3, R4 have the meanings given above and R2 is phenyl or R21- and/or R211-substituted phenyl, can be also obtained as shown in reaction scheme 7 and specified by way of example in the following examples.

In still a further alternative, compounds of formula I, in which R1 is hydrogen, R3 and R4 have the meanings given above and R2 is phenyl or R21- and/or R211-substituted phenyl, can be also obtained as shown in reaction scheme 8 and specified by way of example in the following examples.

Reaction scheme 7:

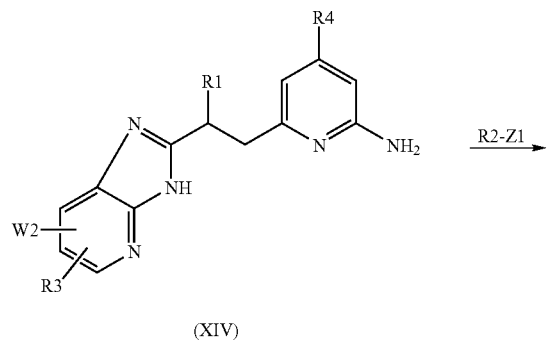

(XIV)

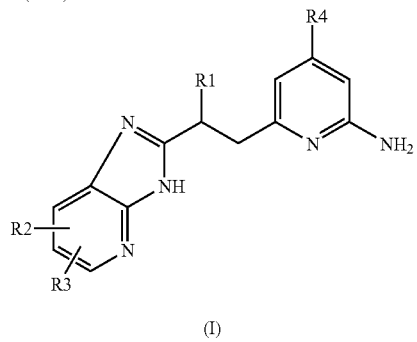

(I)

Reaction scheme 8:

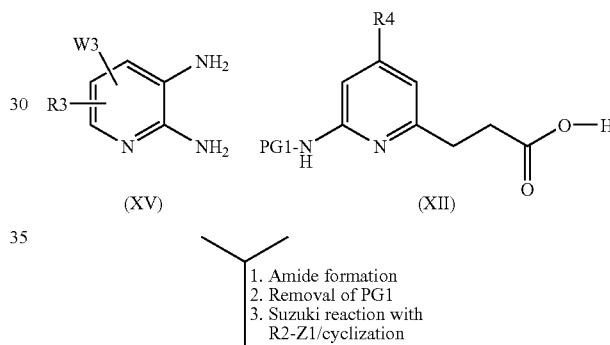

1. Amide formation
2. Removal of PG1
3. Suzuki reaction with R2-Z1/cyclization

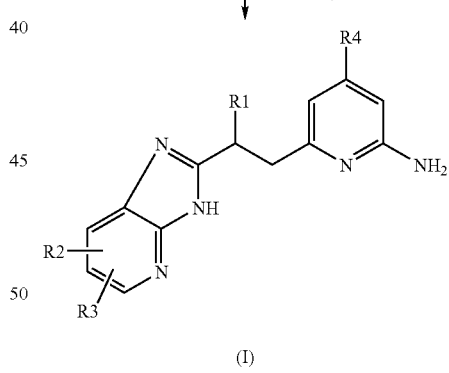

(I)

Compounds of formula XIV, in which R1, R3 and R4 have the meanings mentioned above and W2 is a suitable leaving group (e.g. iodine or bromine), are reacted with boronic acids or boronic acid esters of formula R2-Z1, in which R2 is suitably phenyl or, in particular, R21- and/or R211-substituted phenyl and Z1 is a boronic acid group or a boronic acid ester group, under conditions appropriate for a Suzuki reaction to occur.

Compounds of formula XIV, in which R1, R3 and R4 have the meanings mentioned above and W2 is a suitable leaving group (e.g. iodine or bromine), can be prepared according to the synthesis routes disclosed in this invention or as described in the following examples or analogously or similarly thereto.

As shown in reaction scheme 2, compounds of formula XV, in which R3 has the meanings given above and W3 is a suitable leaving group (e.g. iodine or bromine), can be converted with compounds of formula XII, in which R4 and PG1 has the meanings mentioned above, via amide bond formation reaction, removal of the protective group PG1 and, finally, Suzuki reaction with compounds of formula R2-Z1, in which R2 is phenyl or R21- and/or R211-substituted phenyl and Z1 has the meanings given above, into corresponding compounds of formula I, whereby under the conditions appropriate for the Suzuki reaction to occur simultaneously cyclization takes place.

Suitably, the Suzuki reactions according to this invention are carried out as it is known to the person of ordinary skill in the art and/or in a manner as it is described below and specified by way of example in the following examples or analogously or similarly thereto.

In more detail, the Suzuki reactions mentioned can be carried out in organic solvents alone, for example in toluene, benzene, dimethylformamide or in ethereal (e.g. dimethoxyethane or, in particular, dioxane) or alcohol solvents or in a mixture thereof, or preferably in a mixture comprising an organic solvent (in particular dioxane) and water, with organic (e.g. triethylamine) or preferably inorganic base (e.g. potassium hydroxide, thallium hydroxide, sodium bicarbonate, cesium carbonate, cesium fluoride or potassium carbonate) in the presence of a transition metal catalyst, for example, a nickel or, in particular, palladium catalyst (e.g. $Pd(OAc)_2$, $PdCl_2(PPh_3)_2$, $Pd(PPh_3)_4$) or $PdCl_2(PCy_3)_2$, and, optionally, lithium chloride. The reaction is carried out at a temperature in the range from 20° to 160° C., usually 60° to 130° C. for 10 minutes to 5 days, usually 30 minutes to 24 hours, or 48 to 70 hours. Advantageously, the solvents used are degassed and the reaction is carried out under protective gas.

Boronic acids or boronic acid esters (e.g. pinacol esters) of formula R2-Z1, in which R2 and Z1 have the meanings given above, are known or can be obtained in an art-known manner or analogously or similarly to known compounds. Boronic acid esters (e.g. pinacol esters) of formula R2-Z1 can be prepared, for example, as described in the following examples starting from phenyl triflates or, particularly, phenyl halides, preferably the bromides or iodides, using e.g. bis-(pinacolato)-diboron in the presence of a transition metal, preferably palladium, catalyst. Optionally the boronic acid esters obtained can be isolated or, preferably, they are generated in situ and used in the subsequent Suzuki reaction without isolation.

Compounds of formula XV are known or can be prepared according to known procedures analogously or similarly to the preparation of known compounds.

Compounds of formula I, in which R1, R2 and R3 have the meanings given above and R4 is 1-4C-alkoxy, can be obtained from corresponding compounds of formulae VI and II according to reaction scheme 1 or as described by way of example in the following examples.

Compounds of formula VI, in which PG1 has the meaning mentioned above, e.g. trityl, and R4 is 1-4C-alkoxy, can be obtained from corresponding compounds of formula X according to reaction scheme 3. Compounds of formula X, in which R4 is 1-4C-alkoxy, particularly methoxy, and the moiety $—CO_2R'$ is preferably a methyl ester group, can be obtained according to reaction scheme 9 using the alcohol R4-H. Corresponding steps are described by way of example in the following examples.

Reaction scheme 9:

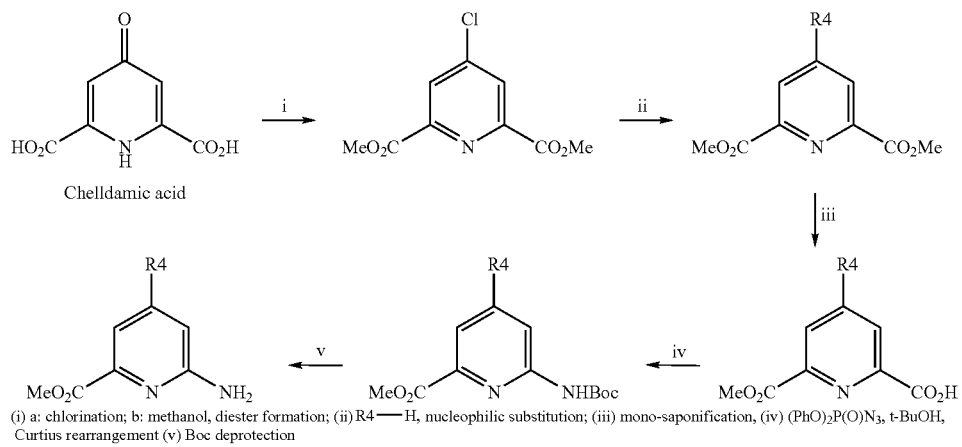

(i) a: chlorination; b: methanol, diester formation; (ii) R4——H, nucleophilic substitution; (iii) mono-saponification, (iv) $(PhO)_2P(O)N_3$, t-BuOH, Curtius rearrangement (v) Boc deprotection It is to be stated, that optionally compounds of formula I can be converted into further compounds of formula I by methods known to one of ordinary skill in the art or as described in the following examples.

More specifically, such as for example, from compounds of formula I, in which

R2 or R3 is bromine or iodine, the corresponding arylated compounds can be obtained by abovementioned Suzuki reaction;

or from compounds of formula I, in which

R21 is benzyloxy, the corresponding free hydroxyl compound can be obtained by debenzylation reaction;

or from compounds of formula I, in which

R2 is phenyl, the corresponding compounds, in which R2 is phenyl substituted by $—SO_2$-Het, can be obtained via two steps by chlorosulfonylation and then reaction with the corresponding heterocyclic amine Het-H.

Optionally, compounds of formula I can be converted into their salts, or, optionally, salts of the compounds of formula I can be converted into the free compounds. Corresponding processes are known to the person skilled in the art.

The compounds of formula I can be converted, optionally, into their N-oxides, for example with the aid of hydrogen peroxide in methanol or with the aid of m-chloroperoxybenzoic acid in dichloromethane. The person skilled in the art is familiar on the basis of his/her expert knowledge with the reaction conditions which are specifically necessary for carrying out the N-oxidation.

It is known to the person skilled in the art that if there are a number of reactive centers on a starting or intermediate compound it may be necessary to block one or more reactive centers temporarily by protective groups in order to allow a reaction to proceed specifically at the desired reaction center. A detailed description for the use of a large number of proven protective groups is found, for example, in T. Greene and P. Wuts, "Protective Groups in Organic Synthesis" (John Wiley & Sons, Inc. 1999, $3^{rd}$ Ed.) or in P. Kocienski, "Protecting Groups (Thieme Foundations Organic Chemistry Series N Group" (Thieme Medical Publishers, 2000).

The substances according to the invention are isolated and purified in a manner known per se, e.g. by distilling off the solvent in vacuo and recrystallizing the residue obtained from a suitable solvent or subjecting it to one of the customary purification methods, such as column chromatography on a suitable support material.

Salts are obtained by dissolving the free compound in a suitable solvent (for example a ketone like acetone, methylethylketone, or methylisobutylketone, an ether, like diethyl ether, tetrahydrofuran or dioxane, a chlorinated hydrocarbon, such as methylene chloride or chloroform, or a low molecular weight aliphatic alcohol, such as ethanol, isopropanol) which contains the desired acid, or to which the desired acid is then added. The salts are obtained by filtering, reprecipitating, precipitating with a non-solvent for the addition salt or by evaporating the solvent. Salts obtained can be converted by basification into the free compounds which, in turn, can be converted into salts. In this manner, pharmacologically non-tolerable salts can be converted into pharmacologically tolerable salts.

Suitably, the conversions mentioned in this invention can be carried out analogously or similarly to methods which are familiar per se to the person skilled in the art, for example, in the manner which is described by way of example in the following examples.

The person skilled in the art knows on the basis of his/her knowledge and on the basis of those synthesis routes, which are shown and described within the description of this invention, how to find other possible synthesis routes for compounds according to this invention. All these other possible synthesis routes are also part of this invention.

Having described the invention in detail, the scope of the present invention is not limited only to those described characteristics or embodiments. As will be apparent to persons skilled in the art, modifications, analogies, variations, derivations, homologisations and adaptations to the described invention can be made on the base of art-known knowledge and/or, particularly, on the base of the disclosure (e.g. the explicite, implicite or inherent disclosure) of the present invention without departing from the spirit and scope of this invention as defined by the scope of the appended claims.

The following examples illustrate the invention in greater detail, without restricting it. As well, further compounds according to the present invention, of which the preparation is explicitly not described, can be prepared in an analogous way or in a way which is known by a person skilled in the art using customary preparation methods and process techniques.

In the examples, m.p. stands for melting point, h for hours, d for days, min for minutes, TLC for thin layer chromatography, Rf for retention factor, MS for mass spectrum, M for molecular ion, other abbreviations have their meanings customary per se for the skilled person.

The compounds which are mentioned in the examples as well as their salts or salt-free forms are preferred compounds of the invention.

EXAMPLES

Final Products 1. 2-[2-(2-Amino-4-methylpyridin-6-yl)ethyl]-3H-imidazo[4,5-b]pyridine 2.27 g of 4-methyl-2-(trityl-amino)-picolinaldehyde (compound A1) and 2.60 g of (3H-imidazo[4,5-b]pyridin-2-yl-methyl)-triphenyl-phosphonium chloride (compound A2) are suspended in a mixture of 41 ml of methanol, 9.1 ml of tetrahydrofuran and 4.5 ml of toluene. 4.60 ml of a solution of sodium methanolate in methanol (1.31 M) are added dropwise. The reaction mixture is stirred at 40° C. for 3.5 h and evaporated to dryness. The resulting residue is chomatographed on silica gel using toluene/ethyl acetate 1:1 to give 3.93 g of a light yellow foam, which is suspended in 78 ml of 50% strength aqueous acetic acid and heated at 80° C. for 0.5 h. The reaction mixture is filtered, rinsed with water, and the filtrate is extracted twice with toluene. The combined organic phases are reextracted twice with water and the combined aqueous phases are evaporated to dryness to give 1.95 g of a yellow, amorphous solid, which is dissolved as obtained in 250 ml of methanol. 2.40 ml of trifluoroacetic acid and 430 mg of palladium on active carbon (10% Pd) are added and the suspension is stirred at room temperature for 3.5 d under hydrogen atmosphere. Then the catalyst is filtered off over kieselguhr and the reaction mixture is conconcentrated to dryness. The residue is dissolved in dichloromethane and washed twice with a mixture of saturated sodium hydrogencarbonate solution/saturated sodium chloride solution (1:1). The organic phase is dried using sodium sulfate and concentrated to dryness. After chromatographical purification of the residue on silica gel (dichoromethane/methanol 8:1, 1% N,N-diisopropylethylamine), evaporation of the eluents and lyophilization from dioxane, 1.20 g of the title compound are obtained as a colorless lyophilisate. M.p. 45°-47° C. MS: 254.1 (MH$^+$). TLC: Rf=0.40 (dichloromethane/methanol 8:1).

1a. 2-[2-(2-Amino-4-methylpyridin-6-yl)ethyl]-3H-imidazo[4,5-b]pyridine hydrochloride 31 mg of 2-[2-(2-Amino-4-methylpyridin-6-yl)ethyl]-3H-imidazo[4,5-b]pyridine (compound 1) are dissolved in 16 ml of dichloromethane. Under ice-cooling, 61 μl of a solution of hydrochloric acid in diethylether (2M strength) are added. The mixture is evaporated to dryness and the residue lyophilized from 15 ml water to give 35 mg of the title compound as colorless lyophilisate. M.p. 136° C. MS: 254.2 (MH$^+$), 528.8 (2MNa$^+$).

1b. 2-[2-(2-Amino-4-methylpyridin-6-yl)ethyl]-3H-imidazo[4,5-b]pyridine acetate 52 mg of 2-[2-(2-Amino-4-methylpyridin-6-yl)ethyl]-3H-imidazo[4,5-b]pyridine (compound 1) are dissolved in 25 ml of dichloromethane. 2 ml of aqueous acetic acid (50% strength) are added. The mixture is concentrated and coevaporated successively with water and dichloromethane to give 65 mg of the title compound as foam. M.p. 54° C. MS: 254.2 (MH$^+$), 528.8 (2MNa$^+$).

2. (R,S)-2-[3-(2-Amino-4-methylpyridin-6-yl)prop-2-yl]-3H-imidazo[4,5-b]pyridine Starting from 4-methyl-2-(trityl-amino)-picolinaldehyde (compound A1) and {1-(3H-imidazo[4,5-b]pyridin-2-yl)-ethyl}-triphenyl-phosphonium chloride (compound A3) the title compound can be obtained as described below or analogously to the procedure as in example 1. M.p. 48° C. MS: 268.1 (MH$^+$). TLC: Rf=0.20 (dichloromethane/methanol 10:1).

944 mg of 4-methyl-2-(trityl-amino)-picolinaldehyde (compound A1) and 1.11 g of {1-(3H-imidazo[4,5-b]pyridin-2-yl)-ethyl}-triphenyl-phosphonium chloride (compound A3) are suspended in a mixture of 17.0 ml of methanol, 3.6 ml of tetrahydrofuran and 2.1 ml of toluene. 1.9 ml of a solution of sodium methanolate in methanol (1.31 M) are added dropwise. The reaction mixture is stirred at 60° C. for 5 h and evaporated to dryness. The resulting residue is chomatographed on silica gel using toluene/ethyl acetate 1:1 to give 1.5 g of a light yellow foam, which is suspended in 30 ml of 50% strength aqueous acetic acid and heated at 80° C. for 0.5 h. The reaction mixture is filtered, rinsed with water, and the filtrate is extracted twice with toluene. The combined organic phases are reextracted twice with water and the combined aqueous phases are evaporated to dryness to give 501 mg of a yellow, amorphous solid, which is dissolved as obtained in 173 ml of methanol. 1.97 ml of trifluoroacetic acid and 408 mg of palladium on active carbon (10% Pd) are added and the suspension is stirred at room temperature for 2.5 d under hydrogen atmosphere. Then the catalyst is filtered off over kieselguhr and the reaction mixture is conconcentrated to dryness. The residue is dissolved in dichloromethane and washed twice with a mixture of saturated sodium hydrogencarbonate solution/saturated sodium chloride solution (1:1). The organic phase is dried using sodium sulfate and concentrated to dryness. After chromatographical purification of the residue on silica gel (dichoromethane/methanol 8:1, 1% N,N-diisopropylethylamine), evaporation of the eluents and lyophilization from dioxane, 514 mg of the title compound are obtained as a colorless lyophilisate.

3. (R,S)-2-[4-(2-Amino-4-methylpyridin-6-yl)but-2-yl]-3H-imidazo[4,5-b]pyridine A solution of 0.632 g of tributyl-{1-(3H-imidazo[4,5-b]pyridin-2-yl)-propyl}-phosphonium chloride (compound A4) in tetrahydrofuran is added to a suspension of 63 mg of sodium hydride (60% strength suspension in paraffin) in 3.75 ml of tetrahydrofuran. After 15 min stirring, a solution of 0.500 g of 4-methyl-2-(trityl-amino)-picolinaldehyde (compound A1) in tetrahydrofuran is added dropwise and the reaction mixture is heated at 80° C. for 6 h. The mixture is then evaporated to dryness and the resulting residue chomatographed on silica gel using toluene/ethyl acetate 5:1 to give 0.266 g of a light yellow oil, which is suspended in 6 ml of 50% strength aqueous acetic acid and heated at 80° C. for 0.5 h. The reaction mixture is filtered, rinsed with water, and the filtrate is extracted twice with toluene. The combined organic phases are reextracted twice with water and the combined aqueous phases are evaporated to dryness to give 0.146 g of a yellow, waxen solid, which is dissolved as obtained in 19 ml of methanol. 0.21 ml of trifluoroacetic acid and 32 mg of palladium on active carbon (10% Pd) are added and the suspension is stirred at room temperature for 2.5 d under hydrogen atmosphere. Then the catalyst is filtered off and the reaction mixture is conconcentrated to dryness. The residue is dissolved in dichloromethane and washed twice with a mixture of saturated sodium hydrogencarbonate solution/saturated sodium chloride solution (1:1). The organic phase is dried using sodium sulfate and concentrated to dryness. After chromatographical purification of the residue on silica gel (dichoromethane/methanol 8:1), evaporation of the eluents and lyophilization from dioxane, 0.170 g of the title compound are obtained as a hygroscopic lyophilisate. M.p. 164°-166° C. MS: 282.1 (MH$^+$).

TLC: Rf=0.24 (dichloromethane/methanol 10:1).

4. 2-[2-(2-Amino-4-methylpyridin-6-yl)ethyl]-6-bromo-3H-imidazo[4,5-b]pyridine A solution of 1.22 g of (6-bromo-3H-imidazo[4,5-b]pyridin-2-yl-methyl)-tributyl-phosphonium chloride (compound A5) in tetrahydrofuran is added to a suspension of 109 mg of sodium hydride (60% strength suspension in paraffin) in 15.3 ml of tetrahydrofuran. After 15 min stirring, a solution of 0.856 g of 4-methyl-2-(trityl-amino)-picolinaldehyde (compound A1) in tetrahydrofuran is added dropwise and the reaction mixture is heated at 80° C. for 6 h. The mixture is then evaporated to dryness and the resulting residue chomatographed on silica gel using toluene/ethyl acetate 5:1 to give 0.672 g of a yellow solid, which is suspended in 14 ml of 50% strength aqueous acetic acid and heated at 80° C. for 1.5 h. The reaction mixture is filtered, rinsed with water, and the filtrate is extracted twice with toluene. The combined organic phases are reextracted twice with water and the combined aqueous phases are evaporated to dryness to give 0.355 g of a yellow, amorphous solid. 0.300 g of said solid are dissolved in 112 ml of methanol. 0.14 ml of glacial acetic acid and 14 mg of platinum dioxide are added and the suspension is stirred at room temperature for 2.5 d under hydrogen atmosphere. Then the catalyst is filtered off and the reaction mixture is concentrated to dryness. The residue is dissolved in dichloromethane and washed twice with a mixture of saturated sodium hydrogencarbonate solution/saturated sodium chloride solution (1:1). The organic phase is dried using sodium sulfate and concentrated to dryness. After chromatographical purification of the residue on silica gel (dichoromethane/methanol 20:1) and evaporation of the eluents, 0.118 g of the title compound are obtained as an amorphous solid. M.p. M.p. 216° C. ESI-MS: 332.3/334.2 (MH$^+$, 100%/96%). TLC: Rf=0.35 (dichloromethane/methanol 10:1).

In an alternative:

930 mg of 6-[(E)-2-(6-bromo-3H-imidazo[4,5-b]pyridin-2-yl)-vinyl]-4-methyl-pyridin-2-ylamine (compound A11) are suspended in 300 ml of methanol. Subsequently, 805 µl acetic acid and 96 mg of Adam's catalyst [platin(IV) oxide] are added. The suspension is vigorously stirred for 65 h. Thereafter, the solution is passed through kieselguhr, which is rinsed with methanol. The filtrate is evaporated to dryness and the remaining residue (1.20 g) purified by chromatography on silica gel (eluent: dichloromethane/methanol=20:1) to afford 690 mg of the title compound as colorless powder after lyophilization from 15.0 ml dioxane and 3.0 ml water. M.p. 216° C. ESI-MS: 332.1/334.2 (MH$^+$, 97%/100%). TLC: Rf=0.35 (dichloromethane/methanol 10:1).

5. 2-[2-(2-Amino-4-methylpyridin-6-yl)ethyl]-6-phenyl-3H-imidazo[4,5-b]pyridine 350 mg of 2-[2-(amino-4-methylpyridin-6-yl)ethyl]-6-bromo-3H-imidazo[4,5-b]pyridine (compound 4) are dissolved in 5.6 ml of anoxic dioxane under a nitrogen atmosphere. Subsequently, 3.15 ml of an aqueous sodium bicarbonate solution (2.0 M), 193 mg of 2-phenyl-1,3,2-dioxaborinane, and 49 mg of trans-dichloro-bis(tricyclohexylphosphane)palladium-(II) are added. The reaction mixture is refluxed at 110° C. for 46 hours. Thereafter, the volatile components are removed in vacuo and the remaining residue is redissolved in 200 ml of a mixture of water/dichloromethane (1:1). The aqueous phase is extracted twice each with 125 ml of dichloromethane. The organic layer is separated, dried using sodium sulfate, and evaporated to dryness to yield a colorless, crude solid. Subsequently, the residue is purified by flash chromatography on silica gel (eluent: dichloromethane/methanol 8:1) to afford 279 mg of the title compound as a colorless solid of m.p. 230° C. MS: 330.3 (MH$^+$). TLC: Rf=0.34 (dichloromethane/methanol 8:1).

6. 2-[2-(2-Amino-4-methylpyridin-6-yl)ethyl]-6-(4-cyano-phenyl)-3H-imidazo[4,5-b]pyridine 296 mg of 2-[2-(amino-4-methylpyridin-6-yl)ethyl]-6-bromo-3H-imidazo[4,5-b]pyridine (compound 4) are dissolved in 4.74 ml of anoxic dioxane under a nitrogen atmosphere. Subsequently, 2.7 ml of an aqueous sodium bicarbonate solution (2.0 M), 231 mg of benzonitrile-4-boronic acid pinacolester, and 42 mg of trans-dichloro-bis(tricyclohexylphosphane)palladium-(II) are added. The reaction mixture is refluxed at 110° C. for 70 hours. Thereafter, the volatile components are removed in vacuo and the remaining residue is redissolved in 150 ml of a mixture of water/dichloromethane (1:1). The aqueous phase is extracted twice each with 100 ml of dichloromethane. The organic layer is separated, dried using sodium sulfate, and evaporated to dryness to yield a colorless, crude solid. Subsequently, the residue is purified by flash chromatography on silica gel (eluent: dichloromethane/methanol 8:1) to afford 127 mg of the title compound as a colorless solid of m.p. 218° C. MS: 355.3 (MH$^+$). TLC: Rf=0.35 (dichloromethane/methanol 8:1).

7. 2-[2-(2-Amino-4-methylpyridin-6-yl)ethyl]-6-p-tolyl-3H-imidazo[4,5-b]pyridine To a solution of 340 mg of (E,Z)-2-[2-(2-amino-4-methylpyridin-6-yl)vinyl]-6-p-tolyl-3H-imidazo[4,5-b]pyridine (compound A6) in 28 ml of methanol is added 0.308 ml of trifluoroacetic acid and 153 mg of palladium on active carbon (10% Pd). The suspension is vigorously stirred at 50° C. for 4.5 d under a hydrogen atmosphere. Then the catalyst is filtered off and the reaction mixture is conconcentrated to dryness. The residue is dissolved in dichloromethane and washed twice with a mixture of saturated sodium hydrogencarbonate solution/saturated sodium chloride solution (1:1). The organic phase is dried using sodium sulfate and concentrated to dryness. After chromatographical purification of the residue on silica gel (dichoromethane/methanol 8:1) and evaporation of the eluents 52 mg of the title compound are obtained as an oil. MS: 344.4 (MH$^+$). TLC: Rf=0.37 (dichloromethane/methanol 8:1).

7a. 2-[2-(2-Amino-4-methylpyridin-6-yl)ethyl]-6-p-tolyl-3H-imidazo[4,5-b]pyridine hydrochloride 41 mg of 2-[2-(2-amino-4-methylpyridin-6-yl)ethyl]-6-p-tolyl-3H-imidazo[4,5-b]pyridine (compound 7) are dissolved in 8.4 ml of dichloromethane. After cooling the solution to 0° C., 61 µl of hydrochloride in diethyl ether (strength 2.0 M) is added under stirring. Subsequently, the solvents are evaporated in vacuo. The remaining residue is redissolved in petrol ether/dichloromethane (3:1) and concentrated to dryness to afford 40 mg of the title compound as an amorphous powder of m.p. 186° C. MS: 344.4 (MH$^+$). TLC: Rf=0.37 (dichloromethane/methanol 8:1).

Starting from the appropriate starting compounds, which are described below or which can be prepared analogously or similarly to the described compounds in a manner known to the person skilled in the art, the following Examples 8 to 9a are obtained as described below or according to the procedure as in Examples 7 or 7a, and the following Examples 10 to 12 are obtained as described below or in such a way as disclosed in the description of this invention.

8. 2-[2-(2-Amino-4-methylpyridin-6-yl)ethyl]-6-(4-fluoro-phenyl)-3H-imidazo[4,5-b]pyridine (i.e. 6-{2-[6-(4-Fluoro-phenyl)-3H-imidazo[4,5-b]pyridin-2-yl]-ethyl}-4-methyl-pyridin-2-ylamine)

To a solution of 138 mg of 6-{(E,Z)-2-[6-(4-fluoro-phenyl)-3H-imidazo[4,5-b]pyridin-2-yl]-vinyl}-4-methyl-pyridin-2-ylamine (compound A7) in 11 ml of methanol is added 42 µl of trifluoroacetic acid and 35 mg of palladium on active carbon (10% Pd). The suspension is vigorously stirred at 50° C. for 3 d under a hydrogen atmosphere. Subsequent workup according to the procedure described herein for example 7 affords 29 mg of the title compound as an amorphous solid. M.p. 228° C. ESI-MS: 348.3 (MH$^+$). TLC: Rf=0.37 (dichloromethane/methanol 8:1).

9. 2-[2-(2-Amino-4-methylpyridin-6-yl)ethyl]-6-(4-dimethylamino-phenyl)-3H-imidazo[4,5-b]pyridine (i.e. 6-{2-[6-(4-Dimethylamino-phenyl)-3H-imidazo[4,5-b]pyridin-2-yl]-ethyl}-4-methyl-pyridin-2-ylamine)

To a solution of 314 mg of 6-{(E,Z)-2-[6-(4-dimethylamino-phenyl)-3H-imidazo[4,5-b]pyridin-2-yl]-vinyl}-4-methyl-pyridin-2-ylamine (compound A8) in 60 ml of methanol is added 487 µl of trifluoroacetic acid and 140 mg of palladium on active carbon (10% Pd). The suspension is vigorously stirred at 50° C. for 6 d under a hydrogen atmosphere. Subsequent workup according to the procedure described herein for example 7 affords 43 mg of the title compound as a viscous oil. ESI-MS: 373.4 (MH$^+$). TLC: Rf=0.40 (dichloromethane/methanol 8:1).

9a. 2-[2-(2-Amino-4-methylpyridin-6-yl)ethyl]-6-(4-dimethylamino-phenyl)-3H-imidazo[4,5-b]pyridine hydrochloride (i.e. 6-{2-[6-(4-Dimethylamino-phenyl)-3H-imidazo[4,5-b]pyridin-2-yl]-ethyl}-4-methyl-pyridin-2-ylamine hydrochloride)

40 mg of 6-{2-[6-(4-dimethylamino-phenyl)-3H-imidazo[4,5-b]pyridin-2-yl]-ethyl}-4-methyl-pyridin-2-ylamine are dissolved in 8.0 ml of dichloromethane. After cooling the solution to 0° C., 53 µl of hydrochloride in diethyl ether (strength 2.0 M) is added under stirring. Subsequently, the solvents are evaporated in vacuo. The remaining residue is re-dissolved in 4 ml of dioxane containing 0.8 ml each of water and acetonitrile. The solution is lyophilized to yield 43 mg of the title compound. M.p. 142° C. (decomp.) TSP-MS: 373.3 (MH$^+$). TLC: Rf=0.40 (dichloromethane/methanol 8:1).

Compound 10 can be prepared as described below or it can be prepared by a person skilled in the art according to reaction scheme 6 specified above in an art-known manner applying customary preparation methods and similarly to the Examples described explicitly herein starting with reaction of a compound of formula XII, in which PG1 is trityl and R4 is methyl, with compound F4.

10. 2-[2-(2-Amino-4-methylpyridin-6-yl)ethyl]-6-(4-chloro-phenyl)-3H-imidazo[4,5-b]pyridine (i.e. 6-{2-[6-(4-Chloro-phenyl-3H-imidazo[4,5-b]pyridin-2-yl]-ethyl}-4-methyl-pyridin-2-ylamine)

36 mg of N-[2-amino-5-(4-chloro-phenyl)-pyridin-3-yl]-3-(6-amino-4-methyl-pyridin-2-yl)-propionamide (compound A9) are treated with 2 g polyphosphoric acid at 125° C. for 24 h. Subsequent workup according to the procedure described herein for example A6 yields 6 mg of the title compound as a viscous oil after chromatography (dichloromethane/methanol 8:1). ESI-MS: 364.4/366.4 (MH$^+$, 100%/36%). TLC: Rf=0.30 (dichloromethane/methanol 8:1).

10a. 6-{2-[6-(4-Chloro-phenyl)-3H-imidazo[4,5-b]pyridin-2-yl]-ethyl}-4-methyl-pyridin-2-ylamine hydrochloride 6.0 mg of 6-{2-[6-(4-chloro-phenyl)-3H-imidazo[4,5-b]pyridin-2-yl]-ethyl}-4-methyl-pyridin-2-ylamine are dissolved in 1.5 ml of dichloromethane. After cooling the solution to 0° C., 8.0 µl of hydrochloride in diethyl ether (strength 2.0 M) is added under stirring. Subsequently, the solvents are evaporated in vacuo to yield 6.4 mg of the title compound as an amorphous solid M.p. 228-230° C. ESI-MS: 364.4/366.4 (MH$^+$, 100%/29%). TLC: Rf=0.30 (dichloromethane/methanol 8:1).

Compound 11 can be prepared as described below or it can be prepared by a person skilled in the art according to reaction scheme 6 specified above in an art-known manner applying customary preparation methods and similarly to the Examples described explicitly herein starting with reaction of a compound of formula XII, in which PG1 is trityl and R4 is methyl, with art-known 2,3-diamino-5-iodo-pyridine.

11. 2-[2-(2-Amino-4-methylpyridin-6-yl)ethyl]-6-(4-iodo-phenyl)-3H-imidazo[4,5-b]pyridine (i.e. 6-[2-(6-Iodo-3H-imidazo[4,5-b]pyridin-2-yl)-ethyl]-4-methyl-pyridin-2-ylamine)

364 mg N-(2-amino-5-iodo-pyridin-3-yl)-3-(6-amino-4-methyl-pyridin-2-yl)-propionamide (compound A10) are treated with 21 g polyphosphoric acid at 110° C. for 24 h. Subsequent workup according to the procedure described herein for example A6 yields 65 mg. Chromatography on silica gel (eluent: dichloromethane/ethanol 8:1) affords 2.5 mg of the title compound as an amorphous solid. ESI-MS: 380.2 (MH$^+$). TLC: Rf=0.30 (dichloromethane/methanol 8:1).

Compound 12 can be prepared as described below or it can be prepared by a person skilled in the art according to reaction scheme 8 specified above in an art-known manner applying customary preparation methods and similarly to the Examples described explicitly herein starting with reaction of a compound of formula XII, in which PG1 is trityl and R4 is methyl, with art-known 2,3-diamino-5-iodo-pyridine.

12. 2-[2-(2-Amino-4-methylpyridin-6-yl)ethyl]-6-(4-trifluoromethyl-phenyl)-3H-imidazo[4,5-b]pyridine (i.e. 4-Methyl-6-{2-[6-(4-trifluoromethyl-phenyl)-3H-imidazo[4,5-b]pyridin-2-yl]-ethyl}-pyridin-2-ylamine 96 mg N-(2-amino-5-iodo-pyridin-3-yl)-3-(6-amino-4-methyl-pyridin-2-yl)-propionamide (compound A10) is dissolved in 3.0 ml anoxic dioxane under a nitrogen atmosphere. Subsequently, 0.7 ml of an aqueous sodium bicarbonate solution (2.0 M), 52 mg 4-(trifluoromethyl)phenyl-boronic acid, and 14 mg trans-dichloro-bis(tricyclohexylphosphane)palladium-(II) are added. The reaction mixture is refluxed at 110° C. for 20 h. Thereafter, the volatile components are removed in vacuo and the remaining residue is re-dissolved in a mixture of water/dichloromethane (1:1). The aqueous phase is extracted several times with dichloromethane. The organic layer is separated, dried using sodium sulfate, and evaporated to dryness to yield 161 mg of a colourless, crude solid. Subsequently, the residue is purified by flash chromatography on silica gel (eluent: dichloromethane/ethanol 8:1) to afford 52 mg of the title compound. M.p. 170° C. ESI-MS: 398.3 (MH$^+$). TLC: Rf=0.25 (dichloromethane/methanol 8:1).

The following compounds 13 to 15 can be prepared according to the following general procedure A and as described in greater details below.

General Procedure A: 2-[2-(2-Amino-4-methylpyridin-6-yl)ethyl]-6-bromo-3H-imidazo[4,5-b]pyridine (compound 4) is dissolved in anoxic dioxane under a nitrogen atmosphere. Subsequently, an aqueous sodium bicarbonate solution (2.0 M), the corresponding arylboronic acid, and trans-dichloro-bis(tricyclohexylphosphane)palladium-(II) are added. The reaction mixture is refluxed at 110° C.-120° C. for several hours. Thereafter, the volatile components are removed in vacuo and the remaining residue is re-dissolved in a mixture of dichloromethane/water (3:1). The aqueous phase is extracted with dichloromethane. The organic layer is separated, dried using sodium sulfate, and evaporated to dryness. Purification is achieved by recrystallisation as described below.

13. 6-{2-[6-(3-Benzyloxy-phenyl)-3H-imidazo[4,5-b]pyridin-2-yl]-ethyl}-4-methyl-pyridin-2-ylamine The title compound is synthesized according to General Procedure A. 150 mg of 2-[2-(2-amino4-methylpyridin-6-yl)ethyl]-6-bromo-3H-imidazo[4,5-b]pyridine in 7.5 ml dioxane, 1.36 ml Na$_2$CO$_3$ solution, 116 mg of 3-benzyloxyphenylboronic acid, 20 mg of PdCl$_2$(PCy$_3$)$_2$, 120° C. for 48 h, 20 ml of CH$_2$Cl$_2$/H$_2$O, 220 mg of crude title compound is purified by re-crystallization from 6.0 ml isopropyl alcohol to yield 120 mg of the title compound. M.p. 181° C. ESI-MS: 436.3 (MH$^+$). TLC: Rf=0.30 (dichloromethane/methanol 10:1).

14. 6-{2-[6-(3,5-Dichloro-phenyl)-3H-imidazo[4,5-b]pyridin-2-yl]-ethyl}-4-methyl-pyridin-2-ylamine The title compound is synthesized according to General Procedure A. 100 mg of 2-[2-(2-amino-4-methylpyridin-6-yl)ethyl]-6-bromo-3H-imidazo[4,5-b]pyridine in 5.0 ml dioxane, 903 µl Na$_2$CO$_3$ solution, 65 mg of 3,5-dichlorophenylboronic acid, 13 mg of PdCl$_2$(PCy$_3$)$_2$, 120° C. for 64 h. During extraction with 20 ml of CH$_2$Cl$_2$/H$_2$O the title compound starts precipitating in the organic layer. Subsequently, 37 mg of the pure title compound can be obtained as a colorless powder after filtration and lyophilization from 2.0 ml dioxane and 1.0 ml water. M.p. 224° C. ESI-MS: 398.3, 400.2, 402.3 (MH$^+$; 100%, 65%, 13%). TLC: Rf=0.24 (dichloromethane/methanol 10:1).

15. 6-{2-[6-(4-Benzyloxy-phenyl)-3H-imidazo[4,5-b]pyridin-2-yl]-ethyl}-4-methyl-pyridin-2-ylamine The title compound is synthesized according to General Procedure A. 100 mg of 2-[2-(2-amino-4-methylpyridin-6-yl)ethyl]-6-bromo-3H-imidazo[4,5-b]pyridine in 5.0 ml dioxane, 903 µl Na$_2$CO$_3$ solution, 78 mg of 4-benzoxyphenylboronic acid, 13 mg of PdCl$_2$(PCy$_3$)$_2$, 110° C. for 70 h, 20 ml of CH$_2$Cl$_2$/H$_2$O, 120 mg of crude title compound is purified by recrystallization from 5.0 ml isopropyl alcohol to yield 57 mg of the pure title compound as colorless solid. M.p. 225° C. ESI-MS: 436.3 (MH$^+$). TLC: Rf=0.35 (dichloromethane/methanol 10:1).

16. 3-{2-[2-(6-Amino-4-methyl-pyridin-2-yl)-ethyl]-3H-imidazo[4,5-b]pyridin-6-yl}-phenol 110 mg of 6-{2-[6-(3-benzyloxy-phenyl)-3H-imidazo[4,5-b]pyridin-2-yl]-ethyl}-4-methyl-pyridin-2-ylamine (compound 13) and 33 mg palladium on active carbon (10% Pd) are suspended in 12 ml of methanol. The suspension is vigorously stirred at r.t. for 64 h under a hydrogen atmosphere. The suspension is passed through kieselguhr and rinsed with methanol. The filtrate is concentrated to dryness to afford 53 mg of crude product. Purification by HPLC yields 20 mg of the title compound as a colorless solid. M.p. 162° C. ESI-MS: 346.2 (MH$^+$). TLC: Rf=0.17 (dichloromethane/methanol 10:1).

The following compounds 17 to 21 can be prepared according to the following general procedure B and as described in greater details below.

General Procedure B: 4-Methyl-6-[2-(6-phenyl-3H-imidazo[4,5-b]pyridin-2-yl)-ethyl]-pyridin-2-ylamine (compound 5) is dissolved in neat chlorosulfonic acid. The solution is heated for 2 h at 80° C. under a nitrogen atmosphere. Subsequently, the solution is cooled to 0° C. and an excess of corresponding secondary amine is carefully added under stirring. The reaction mixture is allowed to warm up to r.t. while stirring is continued for 18 h. Thereafter, the reaction mixture is diluted by adding dichloromethane and extracted 3 times with water and once with sat. sodium bicarbonate solution. The organic layer is separated, dried using sodium sulfate, and evaporated to dryness. Purification of the crude products is achieved by preparative HPLC:

Prep. HPLC conditions:
Column: Supplier YMC, specification: ODS AQ 75×30, S-5 µm, 12 nm, 40 ml/l
Gradient: CH$_3$CN+4.0% H$_2$O+buffer 30 ml/l–H$_2$O+4% CH$_3$CN+buffer 30 ml/l
Buffer: 63.08 g/l NH$_4$HCO$_2$, 53.20 ml/l HCO$_2$H

17. 6-(2-{6-[4-(Azetidine-1-sulfonyl)-phenyl]-3H-imidazo[4,5-b]pyridin-2-yl}-ethyl)-4-methyl-pyridin-2-ylamine The title compound is synthesized according to General Procedure B. 100 mg of 4-methyl-6-[2-(6-phenyl-3H-imidazo[4,5-b]pyridin-2-yl)-ethyl]-pyridin-2-ylamine in 134 µl ClSO$_3$H, 1.02 ml azetidine, 50 ml dichloromethane, extracted 3 times each with 15 ml of water, 20 ml sat. NaHCO$_3$ solution, 120 mg of crude product, HPLC purification yields 14 mg of title compound as colorless powder after lyophilization from 5 ml dioxane/water 10:1. M.p. 168° C. ESI-MS: 449.3 (MH$^+$). TLC: Rf=0.62 (dichloromethane/methanol 5:1).

18. 4-Methyl-6-(2-{6-[4-(pyrrolidine-1-sulfonyl)-phenyl]-3H-imidazo[4,5-b]pyridin-2-yl}-ethyl)-pyridin-2-ylamine The title compound is synthesized according to General Procedure B. 100 mg of 4-methyl-6-[2-(6-phenyl-3H-imidazo[4,5-b]pyridin-2-yl)-ethyl]-pyridin-2-ylamine in 134 µl ClSO$_3$H, 1.26 ml pyrrolidine, 50 ml dichloromethane, extracted 3 times each with 15 ml of water, 20 ml sat. NaHCO$_3$ solution, 170 mg of crude product, HPLC purification yields 14 mg of title compound as colorless powder after lyophilization from 5 ml dioxane/water 10:1. M.p. 171° C. ESI-MS: 463.3 (MH$^+$). TLC: Rf=0.69 (dichloromethane/methanol 5:1).

19. 4-Methyl-6-(2-{6-[4-(piperidine-1-sulfonyl)-phenyl]-3H-imidazo[4,5-b]pyridin-2-yl}-ethyl)-pyridin-2-ylamine The title compound is synthesized according to General Procedure B. 100 mg of 4-methyl-6-[2-(6-phenyl-3H-imidazo[4,5-b]pyridin-2-yl)-ethyl]-pyridin-2-ylamine in 134 µl ClSO$_3$H, 1.29 ml piperidine, 50 ml dichloromethane, extracted 3 times each with 15 ml of water, 20 ml sat. NaHCO$_3$ solution, 100 mg of crude product, HPLC purification yields 8.3 mg of title compound as powder after lyophilization from 4 ml dioxane/water 6:1. M.p. 233° C. ESI-MS: 477.3 (MH$^+$). TLC: Rf=0.15 (dichloromethane/methanol 10:1).

20. 4-{2-[2-(6-Amino-methyl-pyridin-2-yl)-ethyl]-3H-imidazo[4,5-b]pyridin-6-yl}-N,N-dimethyl-benzenesulfonamide The title compound is synthesized according to General Procedure B. 100 mg of 4-methyl-6-[2-(6phenyl-3H-imidazo[4,5-b]pyridin-2-yl)-ethyl]-pyridin-2-ylamine in 134 µl ClSO$_3$H, 1.71 ml N,N-dimethylamine solution (strength 40% in water), 50 ml dichloromethane, extracted 3 times each with 15 ml of water, 20 ml sat. NaHCO$_3$ solution, 101 mg of crude product, HPLC purification yields 16.4 mg of title compound as powder after lyophilization from 5 ml dioxane/water 6:1. M.p. 157° C. ESI-MS: 437.2 (MH$^+$). TLC: Rf=0.13 (dichloromethane/methanol 10:1).

21. 4-Methyl-6-(2-{6-[4-(4-methyl-piperazine-1-sulfonyl)-phenyl]-3H-imidazo[4,5-b]pyridin-2-yl}-ethyl)-pyridin-2-ylamine The title compound is synthesized according to General Procedure B. 200 mg of 4-methyl-6-[2-(6-phenyl-3H-imidazo[4,5-b]pyridin-2-yl)-ethyl]-pyridin-2-ylamine in 268 µl ClSO$_3$H, 3.38 ml N-methylpiperazine, 100 ml dichloromethane, extracted 3 times each with 30 ml of water, 40 ml sat. NaHCO$_3$ solution, 296 mg of crude product, HPLC purification yields 10 mg of title compound as powder after lyophilization from 5 ml dioxane/water 6:1. M.p. 135° C. ESI-MS: 492.2 (MH$^+$). TLC: Rf=0.48 (dichloromethane/methanol 5:1).

22. 2-[2-(2-Amino-4-methoxypyridin-6-yl)ethyl]-3H-imidazo[4,5-b]pyridinium trifluoroacetate 1.0 g of 4-methoxy-2-(trityl-amino)-picolinaldehyde (compound A12) and 1.3 g of (3H-imidazo[4,5-b]pyridin-2-yl-methyl)-triphenyl-phosphonium chloride (compound A2) are suspended in a mixture of 23.4 ml of methanol and 5.3 ml of tetrahydrofuran. 1.94 ml of sodium methoxide solution in methanol (strength 1.31 M) are added dropwise. The reaction mixture is stirred at room temperature for 4.5 h and, subsequently, evaporated to dryness. The residue is chromatographed on silica gel using toluene/ethyl acetate 1:1 to give 1.93 g of an amorphous solid, which is suspended in 27.4 ml of aqueous acetic acid (50% strength) and heated at 80° C. for 1.3 h. The reaction mixture is filtered, rinsed with water, and the filtrate is extracted twice with toluene. The combined organic phases are reextracted twice with water and the combined aqueous phases are evaporated to dryness to give 463 mg of a yellow, amorphous solid, which is dissolved as obtained in 57 ml of methanol. Subsequently, 505 µl of trifluoroacetic acid and 129 mg of palladium on active carbon (10% Pd) are added and the suspension is stirred at room temperature for 2.5 d under a hydrogen atmosphere. Then the catalyst is filtered off (kieselguhr) and the reaction mixture is concentrated to dryness. The crude product is purified by chromatography (eluent: dichloromethane/methanol 5:1) and lyophilized from 20 ml of acetonitrile and 8 ml of ethanol to afford 385 mg of the title compound as a colorless powder. M.p. 189-191° C. MS: 270.3 (MH$^+$). TLC: Rf=0.36 (dichloromethane/methanol 5:1).

Starting Materials

A1. 4-Methyl-2-(trityl-amino)-picolinaldehyde

A solution of 1.0 g of 4-methyl-2-(trityl-amino)-picolinic acid methyl ester (compound B1) in 35 ml of dry toluene is treated dropwise at −70° C. with 2.9 ml of a 1.5 M solution of diisobutylaluminium hydride in toluene. After 0.5 h 5 ml of diethylether and 2.9 ml of diluted aqueous acetic acid (20% strength) are added. After further 0.5 h the reaction mixture is warmed to room temperature and 29 ml of an aqueous solution of ammonia (25% strength) are added. The colorless precipitate is filtered off with suction and washed with toluene. The filtrate is extracted with brine, the organic phase is dried using sodium sulfate and concentrated to dryness. After purification of the crude product on silica gel (eluent: toluene/ethyl acetate 20:1) and evaporation of the eluents, 0.438 g of the title compound are obtained as a colorless, amorphous solid. M.p. 213° C. MS: 379.1 (MH$^+$). TLC: Rf=0.66 (toluene/acetone 10:1).

A2. (3H-Imidazo[4,5-b]pyridin-2-yl-methyl)-triphenyl-phosphonium chloride 3.18 g of chloromethyl-3H-imidazo[4,5-b]pyridine (G. Cleve et al., Liebigs Ann. Chem. 1971, 747, 158-171) are suspended in 16 ml of N,N-dimethylformamide and 50 ml of acetonitrile. 4.98 g of triphenylphosphine are added and the mixture is heated to 100° C. for 3 h. The mixture is concentrated to dryness and the crude product purified by chromatography on silica gel (eluent: dichloromethane/methanol 10:1 to 8:1) to afford 3.15 g of the title compound as a beige, amorphous solid. M.p. 302° C. MS: 394.3 (M$^+$). TLC: Rf=0.17-0.50 (dichloromethane/methanol 10:1).

A3. {1-(3H-Imidazo[4,5-b]pyridin-2-yl)-ethyl}-triphenyl-phosphonium chloride 8.66 g of 2-(1-chloroethyl)-3H-imidazo[4,5-b]pyridine (compound B2) are suspended in 40 ml of N,N-dimethylformamide and 120 ml of acetonitrile. 12.6 g of triphenylphosphine are added and the mixture is heated to 150° C. for 17 h. The mixture is concentrated to dryness and the crude product purified by chromatography on silica gel (eluent: dichloromethane/methanol 20:1) to afford 4.16 g of the title compound as an oil. MS: 408.0 (M$^+$). TLC: Rf=0.22-0.47 (dichloromethane/methanol 10:1).

A4. Tributyl-(1-(3H-imidazo[4,5-b]pyridin-2-yl)-propyl)-phosphonium chloride 8.66 g of 2-(1-chloropropyl)-3H-imidazo[4,5-b]pyridine (compound B3) are suspended in 18 ml of N,N-dimethylformamide and 61 ml of acetonitrile. 6.3 ml of triphenylphosphine are added at 40° C. and the mixture is heated to 90° C. for 16 h. The mixture is concentrated to dryness to give 11.9 g of the title compound as an oil, which is used as obtained. MS: 362.2 (M$^+$). TLC: Rf=0.26-0.43 (dichloromethane/methanol 10:1).

A5. (6-Bromo-3H-imidazo[4,5-b]pyridin-2-yl-methyl)-tributyl-phosphonium chloride 4.0 g of 6-bromo-2-chloromethyl-3H-imidazo[4,5-b]pyridine (compound B4) are suspended in 16 ml of N,N-dimethylformamide and 54 ml of acetonitrile. 4.9 ml of triphenylphosphine and 0.599 g of tetrabutylammonium iodide are added sequentially at 40° C. and the mixture is heated to 90° C. for 20 h. The mixture is concentrated to dryness to give the 8.94 g of the crude title compound as an oil, which is used as obtained. MS: 412.3, 414.2 (M$^+$). TLC: Rf=0.40-0.55 (dichloromethane/methanol 10:1).

A6. (E,Z)-2-[2-(2-Amino-4-methylpyridin-6-yl)vinyl]-6-p-tolyl-3H-imidazo[4,5-b]pyridine 436 mg of (E,Z)-3-N-[(2-amino-4-methylpyridin-6-yl)-propen-1-on-3-yl)-2,3-diamino-5p-tolyl-pyridine amide (compound B5) are treated with 17 g polyphosphoric acid at 125° C. for 24 h. Thereafter, 190 ml of water are carefully added at 100° C. under continuous stirring. Subsequently, the solution is cooled to room temperature and treated with 35 ml of an aqueous sodium hydroxide solution (strength 9.0 M) adjusting pH=7. The neutral solution is extracted four times each with 100 ml of ethyl acetate. The combined organic phases are reextracted twice each using 80 ml of brine, subsequently dried using sodium sulfate, filtered with suction, and concentrated in vacuo to obtain 340 mg of the title compounds as an amorphous solid. MS: 342.4 (MH$^+$). TLC: Rf=0.53 (dichloromethane/methanol 8:1).

A7. 6-{(E,Z)-2-[6-(4-Fluoro-phenyl)-3H-imidazo[4,5-b]pyridin-2-yl]-vinyl}-4-methyl-pyridin-2-ylamine 285 mg of (E,Z)-N-[2-amino-5-(4-fluoro-phenyl)-pyridin-3-yl]-3-(6-amino4-methylpyridin-2-yl)-acrylamide (compound B6) are treated with 12 g polyphosphoric acid at 125° C. for 24 h. Subsequent workup according to the procedure described herein for example A6 yields 146 mg of the title compound as an amorphous solid. TSP-MS: 346.1 (MH$^+$). TLC: Rf=0.47 (dichloromethane/methanol 8:1).

A8. 6-{(E,Z)-2-[6-(4-Dimethylamino-phenyl)-3H-imidazo[4,5-b]pyridin-2-yl]-vinyl}-4-methyl-pyridin-2-ylamine 533 mg of (E,Z)—N-[2-amino-5-(4-dimethylamino-phenyl)pyridin-3-yl]-3-(6-amino-4-methyl-pyridin-2-yl)-acrylamide (compound B7) are treated with 21 g polyphosphoric acid at 125° C. for 24 h. Subsequent workup according to the procedure described herein for example A6 yields 324 mg of the title compound as an amorphous solid. ESI-MS: 371.4 (MH$^+$). TLC: Rf=0.46 (dichloromethane/methanol 8:1).

A9. N-[2-Amino-5-(4-chloro-phenyl)-pyridin-3-yl]-3-(6-amino-4-methyl-pyridin-2-yl)-propionamide 405 mg of N-[2-amino-5-(4-chloro-phenyl)-pyridin-3-yl]-3-[4-methyl-6-(trityl-amino)-pyridin-2-yl]-propionamide (compound B8) are dissolved in 24 ml of aqueous acetic acid (50% strength) and heated at 80° C. for 3 h. Subsequent workup according to the procedure described herein for example B5 yields 36 mg of the title compound as an oil. ESI-MS: 382.2/384.2 (MH$^+$, 100%/36%). TLC: Rf=0.40 (dichloromethane/methanol 10:1).

A10. N-(2-Amino-5-iodo-pyridin-3-yl)-3-(6-amino-4-methyl-pyridin-2-yl)-propionamide 672 mg of N-(2-amino-5-iodo-pyridin-3-yl)-3-[4-methyl-6-(trityl-amino)-pyridin-2-yl]-propion-amide (compound B9) are dissolved in 13 ml of aqueous acetic acid (50% strength) and heated at 80° C. for 4 h. Subsequent workup according to the procedure described herein for example B5 yields 116 mg of the title compound as an oil after chromatography on silica gel (eluent: dichloromethane/methanol 8:1). ESI-MS: 398.0 (MH⁺). TLC: Rf=0.32 (dichloromethane/methanol 8:1).

A11. 6-[(E)-2-(6-Bromo-3H-imidazo[4,5-b]pyridin-2-yl)-vinyl]-4-methyl-pyridin-2-ylamine 1.20 g of N-{6-[(E)-2-(6-bromo-3H-imidazo[4,5-b]pyridin-2-yl)-vinyl]-4-methyl-pyridin-2-yl}-acetamide (compound B10) are suspended in 12 ml of aqueous sulphuric acid (10% strength) at 115° C. for 17 h. Subsequently, the mixture is cooled to 0° C. and conc. aqueous ammonia is added until pH=10. Thereafter, the mixture is extracted 3 times each with 70 ml of ethyl acetate. The combined organic layers are dried using sodium sulphate, filtered with suction, and evaporated to dryness to yield 880 mg of the title compound as an oil, which solidifies upon standing. M.p. 280° C. ESI-MS: 330.2/332.2 (MH⁺; 100%/90%). TLC: Rf=0.35 (dichloromethane/methanol 10:1).

A12. 4-Methoxy-2-(trityl-amino)-picolinaldehyde 1.19 g of methyl 4-methoxy-2-(trityl-amino)-picolinic acid (compound B12) are dissolved in 41 ml of toluene. Subsequently, the solution is cooled to −70° C. and 3.36 ml of diisobutylaluminium hydride in toluene (strength 1.5 M) are added dropwise. After 30 min, 6.0 ml of diethyl ether and 3.5 ml of aqueous acetic acid (20% strength) are added. After further 30 min, the mixture is allowed to warm up to room temperature. Subsequently, 34 ml of aqueous ammonia (25% strength) is added and the mixture is filtered through a celite pad. The filter cake is rinsed with 50 ml of toluene. The filtrate is extracted three times each with 70 ml of sat sodium chloride solution. The organic layer is dried using sodium sulphate, filtered with suction and concentrated in vacuum. The crude product (1.36 g) is purified by chromatography (eluent: toluene/ethyl acetate 10:1) to yield 898 mg of the title compound as an amorphous solid. M.p. 172° C. TSP-MS: 395.2 [MH⁺]. TLC: $R_f$=0.40 (toluene/ethyl acetate 10:1).

B1. 4-Methyl-2-(trityl-amino)-picolinic acid methyl ester

A solution of 40.0 g of 2-acetylamino-4,6-dimethyl-pyridine (M. Belcher, J. Am. Chem. Soc. 1952, 74, 1916-1918) in a mixture of 127 ml of tert-butanol and 375 ml of water is treated portionwise (max 3.0 g each) over a period of 3.5 h at 75° C. with 92 g of potassium permanganate. After completion of the addition, the reaction mixture is heated at 80° C. for 3 h. Afterwards, the reaction mixture is filtered over celite and the filter cake is rinsed with 100 ml of water. Under cooling unreacted 2-acetylamino-4,6-dimethyl-pyridine precipitates from the filtrate and is filtered off with suction. The mother liquor is concentrated to ¼ of its volume and adjusted to pH 5 with the aid of 13.0 ml of concentrated hydrochloric acid. The precipitate is filtered off, dried, dissolved in 300 ml of methanolic hydrochloric acid (2.2 M strength) and heated at 80° C. for 15 h. After evaporation to dryness, the residue is dissolved in 200 ml of water, 100 ml of dichloromethane are added and the mixture is neutralized by addition of sodium hydrogencarbonate. The phases are separated and the water phase is reextracted twice each with 200 ml of dichloromethane. The combined organic phases are dried using sodium sulfate and concentrated to dryness to give 12.1 g of crude 2-amino-4-methyl-picolinic acid methyl ester, which is dissolved in 180 ml of dichloromethane and treated with 22.2 g of trityl chloride and 15 ml of N,N-diisopropylethylamine. After 16 h the reaction mixture is extracted with a mixture of saturated sodium hydrogencarbonate solution/saturated sodium chloride solution (1:1), the organic phase is dried over sodium sulfate and the solvents are evaporated. The crude product is purified by chromatography (eluent: toluene/ethyl acetate 15:1) on silica gel to give 18.5 g of the title compound as a colorless foam. MS: 409.1 (MH⁺). TLC: Rf=0.37 (toluene/acetone 10:1).

B2. 2-(1-Chloroethyl)-3H-imidazo[4,5-b]pyridine 5.2 g of 2,3-diaminopyridine in 209 g of polyphosphoric acid are heated at 120° C. for 0.5 h. The solution is cooled to 80° C. and 4.6 ml of 2-chloropropionitrile are added. Thereafter, the reaction mixture is heated to 180° C. for 2.5 h. After cooling, the polyphosphoric acid is hydrolysed with 150 ml of water. After reheating to 90° C., charcoal is added under vigorous stirring. Subsequently, the suspension is filtered through a celite pad while still hot (70° C.). The filter cake is rinsed with 100 ml of water and the pH value of the filtrate is adjusted to pH 4 using 9 M aqueous sodium hydroxide solution. The mixture is extracted twice each with 250 ml of ethyl acetate, the combined organic phases are dried using sodium sulfate, concentrated and lyophilized from ethanol/water to give 3.56 g of the title compound as a light brown, amorphous solid. MS: 182.2/184.2 (MH⁺, 100%/32%). M.p. 132° C. TLC: Rf=0.60 (dichloromethane/methanol 8:1).

B3. 2-(1-Chloropropyl)-3H-imidazo[4,5-b]pyridine 5.0 g of 2,3-diaminopyridine in 200 g of polyphosphoric acid are heated at 120° C. for 0.5 h. The solution is cooled to 80° C. and 5.7 ml of 2-chlorobutyric acid are added. Thereafter, the reaction mixture is heated to 130° C. for 22 h. After cooling, the polyphosphoric acid is hydrolysed with 136 ml of water. After reheating to 90° C., charcoal is added under vigorous stirring. Subsequently, the suspension is filtered through a celite pad while still hot (70° C.). The filter cake is rinsed with 100 ml of water and the pH 4 using 9 M aqueous sodium hydroxide solution. The mixture is extracted three times each with 200 ml of ethyl acetate, the combined organic phases are dried using sodium sulfate, concentrated and purified by chromatography on silica gel (eluent: toluene/ethyl acetate 1:1) to give 5.19 g of the title compound as a colorless, amorphous solid. M.p. 137° C. MS: 196.0/198.0 (MH⁺, 100%/32%). TLC: Rf=0.50 (dichloromethane/methanol 10:1).

B4. 6-Bromo-2-chloromethyl-3H-imidazo[4,5-b]pyridine 3.0 g of 5-bromo-2,3-diaminopyridine (S.—X. Cai et al., J. Med. Chem. 1997, 40(22), 3679-3686) in 120 g of polyphosphoric acid are heated at 160° C. for 0.5 h. The solution is cooled to 100° C. and 1.26 ml of chloroacetonitrile are added. Thereafter, the reaction mixture is heated to 170° C. for 22 h. After cooling, the polyphosphoric acid is hydrolysed with 81 ml of water. After reheating to 90° C., charcoal is added under vigorous stirring. Subsequently, the suspension is filtered through a celite pad while still hot (70° C.). The filter cake is rinsed with 85 ml of water and the pH 4 using 9 M aqueous sodium hydroxide solution. The precipitate is collected, suspended in 100 ml of hot methanol and filtered over celite. The filtrate is concentrated to dryness to afford 2.78 g of the title compound as a beige, amorphous solid. M.p. >325° C. MS: 246.2/248.2/250.3 (MH⁺, 77%/100%/25%). TLC: Rf=0.42 (dichloromethane/methanol 10:1).

B5. (E,Z)-3-N-[(2-Amino-4-methylpyridin-6-yl)-propen-1-on-3-yl)-2,3-diamino-5-p-tolyl-pyridine amide 1.30 g of (E,Z)-3-N-{[4-methyl-(2-trityl-amino)-pyridin-6-yl]-propen-1-on-3-yl}-2,3-diamino-5-p-tolyl-pyridine amide (compound C1) are dissolved in 75 ml of aqueous acetic acid (50% strength) and heated at 80° C. for 2 h. Subsequently, the resulting colorless precipitate is filtered off and rinsed with water. The filtrate is concentrated to dryness and coevaporated twice each with 20 ml of toluene. The residue is purified by chromatography on silica gel (eluent: dichloromethane/methanol 10:1) to yield 436 mg of the title compounds after evaporation of eluents as a colorless oil. MS: 360.2 (MH$^+$), 718.9 (2MH$^+$). TLC: Rf=0.15 (dichloromethane/methanol 10:1).

B6. (E,Z)—N-[2-Amino-5-(4-fluoro-phenyl)-pyridin-3-yl]-3-(6-amino-4-methyl-pyridin-2-yl)-acrylamide 1.60 g of (E,Z)—N-[2-amino-5-(4-fluoro-phenyl)-pyridin-3-yl]-3-[4-methyl-6-(trityl-amino)-pyridin-2-yl]-acrylamide (compound C2) are dissolved in 95 ml of aqueous acetic acid (50% strength) and heated at 80° C. for 2 h. Subsequent workup according to the procedure described herein for example B5 yields 294 mg of the title compound as an amorphous solid. ESI-MS: 364.1 (MH$^+$). TLC: Rf=0.45 (dichloromethane/methanol 10:1).

B7. (E,Z)—N-[2-Amino-5-(4-dimethylamino-phenyl)-pyridin-3-yl]-3-(6-amino-4-methyl-pyridin-2-yl)-acrylamide 1.14 g of (E,Z)—N-[2-amino-5-(4-dimethylamino-phenyl)-pyridin-3-yl]-3-[4-methyl-6-(trityl-amino)-pyridin-2-yl]-acrylamide (compound C3) are dissolved in 65 ml of aqueous acetic acid (50% strength) and heated at 80° C. for 1.5 h. Subsequent workup according to the procedure described herein for example B5 yields 543 mg of the title compound as an amorphous solid. ESI-MS: 389.2 (MH$^+$). TLC: Rf=0.29-0.43 (dichloromethane/methanol 10:1).

B8. N-[2-Amino-5-(4-chloro-phenyl)-pyridin-3-yl]-3-[4-methyl-6-(trityl-amino)-pyridin-2-yl]-propionamide 300 mg of 3-[4-methyl-6-(trityl-amino)-pyridin-2-yl]-propionic acid (compound C4) and 156 mg of 2,3-diamino-5-(4-chloro-phenyl)-pyridine (compound F4) are dissolved in 13 ml of pyridine and sequentially treated with 280 mg of O-[(ethoxycarbonyl)canomethylene-amino]—N,N,N',N'-tetramethyl-uronium tetrafluoroborate and 153 µl of diisopropylethyl amine. The reaction mixture is warmed to 40° C. for 120 h. Purification of the crude product by chromatography on silica gel (eluent: dichloromethane/methanol 8:1) afforded 405 mg of the title compound as an oil. ESI-MS: 624.1/626.1 (MH$^+$, 100%/38%). TLC: Rf=0.32 (dichloromethane/methanol 8:1).

B9. N-(2-Amino-5-iodo-pyridin-3-yl)-3-[4-methyl-6-(trityl-amino)-pyridin-2-yl]-propionamide 1.30 g of 3-[4-methyl-6-(trityl-amino)-pyridin-2-yl]-propionic acid acid and 724 mg of 2,3-diamino-5-iodo-pyridine are dissolved in 37 ml of pyridine and sequentially treated with 1.06 g of O-[(ethoxycarbonyl)canomethylene-amino]—N,N,N',N'-tetramethyl-uronium tetrafluoro-borate and 579 µl of diisopropylethyl amine. The reaction mixture is warmed to 50° C. for 24 h. Thereafter the solvents are evaporated in vacuo. The remaining residue is coevaporated twice with toluene yielding 3.55 g of crude product. Purification by chromatography on LiChroprep® NH$_2$ (25-40 µm, Merck, Darmstadt) (75 g, eluent: toluene/ethyl acetate 1:1) affords 1.08 g of the title compound as an amorphous solid. ESI-MS: 640.0 (MH$^+$). TLC: Rf=0.16 (toluene/ethyl acetate 1:1, LiChroprep® NH$_2$ HPTLC).

B10. N-{6-[(E)-2-(6-Bromo-3H-imidazo[4,5-b]pyridin-2-yl)-vinyl]-4-methyl-pyridin-2-yl}-acetamide 5.0 g of 6-brom-3H-imidazo[4,5-b]pyridin-2-yl-methyl}-tributyl-phosphonium-chlorid (compound A5) are suspended in 50 ml of tetrahydrofuran and added to a suspension of sodium hydride (60% strength) in 50 ml tetrahydrofuran at room temperature. After vigorously stirring for 10 min, 1.43 g of N-(6-formyl-4-methyl-pyridin-2-yl)-acetamide (compound B11) is added in portions (10 min). Subsequently, the suspension is heated at 90° C. for 22 h. Thereafter, the mixture is filtered with suction and the remaining residue is rinsed with tetrahydrofuran. The pure title compound is obtained by evaporating the filtrate to dryness to afford 1.88 g of an amorphous solid. M.p.>350° C. ESI-MS: 372.1/374.1 (MH$^+$; 99%/100%). TLC: Rf=0.50 (dichloromethane/methanol 10:1).

B11. 3-(6-Acetylamino-4-methyl-pyridin-2-yl)-propionic acid 6.15 g of 3-(6-acetylamino-4-methyl-pyridin-2-yl)-propionic acid methyl ester (compound C5) is dissolved in 100 ml methanol and 70 ml water. Subsequently, 30.44 ml of a 1.0 M solution of NaOH is added while stirring is continued for 18 h at r.t. 2.0 g of amberlite IR-120 [H$^+$] is added and the suspension is stirred for 10 min to neutralize the reaction mixture. The ion exchange resin is removed by filtration and 7.1 g of the crude product is isolated as a colourless solid after evaporation of solvent. Purification by chromatography on silica gel (eluent: dichloromethane/ethanol 10:1) affords 5.32 g of the title compound. M.p. 202° C. ESI-MS: 223.1 (MH$^+$). TLC: Rf=0.13 (cyclohexane/ethyl acetate 1:1+1.0 vol % acetic acid).

B12. Methyl 4-methoxy-2-(trityl-amino)-picolinic acid 1.70 g of methyl 2-amino-4-methoxy-picolinic acid (compound C6) are dissolved in 44 ml of dichloromethane. Subsequently, 1.92 ml of diisopropylethylamine, 690 mg of tetrabutylammonium iodide, and 3.12 g of trityl chloride are added. The solution is stirred for 48 h at room temperature. Thereafter, the mixture is extracted three times each with 50 ml of sat sodium hydrogencarbonate solution. The organic layer is dried using sodium sulphate, filtered with suction and concentrated in vacuum. The crude product (5.38 g) is purified by chromatography (eluent: toluene/ethyl acetate 5:1) to afford 3.49 g of the title compound as a colorless oil. TSP-MS: 425.2 [MH$^+$]. TLC: R$_f$=0.37 (toluene/ethyl acetate 5:1).

C1. (E,Z)-3-N-{[4-Methyl-(2-trityl-amino)-pyridin-6-yl]-propen-1-on-3-yl}-2,3-diamino-5-p-tolyl-pyridine amide 1.20 g of (E,Z)-4-methyl-2-(trityl-amino)-pyridine-6-(propen-3-ylic) acid (compound D1) and 568 mg of 2,3-diamino-5-p-tolyl-pyridine (compound F1) are dissolved in 53 ml of pyridine and sequentially treated with 1.12 g of O-[(ethoxycarbonyl)canomethylene-amino]—N,N,N',N'-tetramethyluronium tetra-fluoroborate and 0.611 ml of diisopropylethyl amine. The reaction mixture is warmed to 65° C. for 24 h. After completion of the amide formation (TLC), the solution is concentrated in vacuo and coevaporated three times each with 20 ml of toluene. The crude product is purified by chromatography on silica gel (eluent: dichloromethane/methanol 15:1) to afford 1.30 g of the title compounds as colorless oil. MS: 602.3 (MH$^+$). TLC: Rf=0.45-0.47 (dichloromethane/methanol 10:1).

C2. (E,Z)-N-[2-Amino-5-(4-fluoro-phenyl)-pyridin-3-yl]-3-[4-methyl-6-(trityl-amino)-pyridin-2-yl]-acrylamide 1.20 g of (E,Z)-4-methyl-2-(trityl-amino)-pyridine-6-(propen-3-ylic) acid (compound D1) and 580 mg of 2,3-diamino-5-(4-fluoro-phenyl)-pyridine (compound F2) are dissolved in 54 ml of pyridine and sequentially treated with 1.08 g of O-[(ethoxycarbonyl)canomethylene-amino]-N,N,N',N'-tetramethyl-uronium tetrafluoroborate and 586 μl of diisopropylethyl amine. The reaction mixture is warmed to 70° C. for 44 h. Purification of the crude product by chromatography on silica gel (eluent: dichloromethane/methanol 15:1) afforded 1.63 g of the title compound as an amorphous solid. ESI-MS: 606.2 (MH$^+$). TLC: Rf=0.47 (dichloromethane/methanol 10:1).

C3. (E,Z)—N-[2-Amino-5-(4-dimethylamino-phenyl)-pyridin-3-yl]-3-[4-methyl-6-(trityl-amino)-pyridin-2-yl]-acrylamide 850 mg of (E,Z)-4-methyl-2-(trityl-amino)-pyridine-6-(propen-3-ylic) acid (compound D1) and 462 mg of 2,3-diamino-5-(4-N,N-dimethylaminophenyl)-pyridine (compound F3) are dissolved in 45 ml of pyridine and sequentially treated with 696 mg of O-[(ethoxycarbonyl)canomethylene-amino]—N,N,N',N'-tetramethyl-uronium tetrafluoroborate and 586 μl of diisopropylethyl amine. The reaction mixture is warmed to 50° C. for 24 h. Purification of the crude product by chromatography on silica gel (eluent: dichloromethane/methanol 15:1) afforded 1.14 g of the title compound as an amorphous solid. ESI-MS: 631.1 (MH$^+$). TLC: Rf=0.60-0.70 (dichloro-methane/methanol 10:1).

C4. 3-[4-Methyl-6-(trityl-amino)-pyridin-2-yl]-propionic acid 1.80 g of (E,Z)-4-methyl-2-(trityl-amino)-pyridine-6-(propen-3-ylic) acid (compound D1) and 180 mg palladium on active carbon (10% Pd) are suspended in 100 ml of methanol. The suspension is vigorously stirred at r.t. for 19 h under a hydrogen atmosphere. Then the catalyst is filtered off over kieselguhr and rinsed with methanol. The filtrate is concentrated to dryness to afford 1.63 g of the title compound as a colourless powder. ESI-MS: 423.1 (MH$^+$). TLC: Rf=0.45 (dichloromethane/methanol 10:1).

C5. 3-(6-Acetylamino-4-methyl-pyridin-2-yl)-propionic acid methyl ester 6.2 g (E)-3-(6-acetylamino-4-methyl-pyridin-2-yl)-acrylic acid methyl ester (compound D2) are dissolved in 250 ml of ethyl acetate. Subsequently, 1.86 g palladium on active carbon (10% Pd) are added. The suspension is vigorously stirred at r.t. for 14 h under a hydrogen atmosphere. Then the catalyst is removed by filtration over kieselguhr and rinsed with ethyl acetate. The filtrate is concentrated to dryness to afford 6.16 g of the title compound as a colourless solid. M.p. 82° C. ESI-MS: 237.1 (MH$^+$). TLC: Rf=0.18 (cyclohexane/ethyl acetate 2:1).

C6. Methyl 2-amino-4-methoxy-picolinic acid 2.87 g of methyl 2-tert-butyloxycarbonylamino-4-methoxy-pyridin-6-carboxylic acid (compound D3) are dissolved in 72 ml of formic acid. Subsequently, the solution is warmed to 40° C. for 2.5 h. After completion of the reaction, the solution is concentrated in vacuum and coevaporated with toluene. The remaining residue is redissolved in 150 ml of dichloromethane and extracted three times each with 50 ml of sat sodium hydrogencarbonate solution. The organic layer is dried using sodium sulphate, filtered with suction and concentrated in vacuum to yield 1.85 g of the title compound as a colorless oil. ESI-MS: 183.1 [MH$^+$]. TLC: R$_f$=0.28 (dichloromethane/methanol 10:1).

D1. (E,Z)-[4-Methyl-2-(trityl-amino)-pyridin-6-yl]-propen-3-ylic acid 1.62 g of (E,Z)-[4-methyl-2-(trityl-amino)-pyridin-6-yl]-propen-3-ylic acid methyl ester (compound E1) are dissolved in 70 ml of tetrahydrofuran. Subsequently, 37.3 ml of a 1.0 M solution of aqueous sodium hydroxide are added and the reaction mixture is warmed to 50° C. for 27 h. At room temperature 22 g of amberlite IR-120 [H$^+$] are added and the suspension is stirred for 15 min neutralizing the reaction mixture. The ion exchange resin is removed by filtration and 1.19 g of the title compounds are isolated as a colorless solid after evaporation of solvent of m.p. 147° C. MS: 421.0 (MH$^+$).

TLC: Rf=0.45 (dichloromethane/methanol 10:1).

D2. (E)-3-(6-Acetylamino-4-methyl-pyridin-2-yl)-acrylic acid methyl ester

The title compound can be synthesized analogously to the procedure described for example E1: 6.0 g of N-(6-formyl-4-methyl-pyridin-2-yl)-acetamide (compound E2) and 10.62 g of methyl diethyl phosphonoacetate in the presence of 1.75 g NaH (60% strength suspension in paraffin); yield after a reaction time of 15 h and chromatography on silica gel (eluent; cyclohexane/ethyl acetate 2:1) 6.22 g of (E)-3-(6-acetylamino-4-methyl-pyridin-2-yl)-acrylic acid methyl ester as a colourless solid. M.p. 139° C. ESI-MS: 235.1 (MH$^+$). TLC: Rf=0.35 (cyclohexane/ethyl acetate 2:1).

D3. Methyl 2-tert-butyloxycarbonylamino-4-methoxy-pyridin-6-carboxylic acid 2.0 g of methyl 4-methoxy-pyridin-2,6-dicarboxylic acid (compound E3) are suspended in 40 ml of dioxane and 5.63 ml of tert-butanol. 2.63 ml of triethylamine and 4.08 ml of diphenylphosphoryl azide are added to the mixture. Subsequently, the reaction mixture is heated at 80° C. for 72 h with vigorous stirring under a nitrogen atmosphere. Further 0.41 ml each of diphenylphosphoryl azide are added after 24 h and 48 h, respectively. Thereafter, the mixture is cooled to room temperature, diluted with 300 ml of ethyl acetate and extracted four times each with 80 ml of sat sodium hydrogencarbonate. The organic layer is dried using sodium sulphate, filtered with suction and concentrated in vacuum. The crude product (5.08 g) is purified by chromatography (eluent: toluene/ethyl acetate 5:1) to afford 1.10 g of the title compound as a colorless oil. TSP-MS: 283.1 [MH$^+$]. TLC: R$_f$=0.24 (toluene/ethyl acetate 5:1).

E1. (E,Z)-[4-methyl-2-(trityl-amino)-pyridin-6-yl-]-propen-3-ylic acid methyl ester Under ice-cooling, a suspension of 190 mg of sodium hydride (60% strength suspension in paraffin) in 15 ml of tetrahydrofuran is treated with a solution of 1.78 g of methyl diethyl phosphonoacetate in 7.6 ml of tetrahydrofuran. After stirring at 0° C. for 30 min, a suspension of 2.3 g of 4-methyl-2-(trityl-amino)-picolinaldehyde (compound A1) in 15 ml of tetrahydrofuran is added. The reaction mixture is stirred for 70 h at room temperature. Thereafter, the mixture is treated with 20 ml of a saturated aqueous ammonium chloride solution for 30 min. The solution is diluted with 30 ml of water and extracted three times each with 50 ml of diethyl ether. The organic layer is separated, dried using sodium sulfate, filtered with suction, and concentrated in vacuo to yield a crude oil of the title compound. After chromatographical purification of the residue on silica gel (toluene/ethyl acetate 20:1) and evaporation of the eluents, 6.6 g of the title compounds are obtained as a colorless oil. MS: 435.0 (MH$^+$). TLC: Rf=0.45 (toluene/ethyl acetate 20:1).

E2. N-(6-Formyl-4-methyl-pyridin-2-yl)-acetamide 5.0 g N-(4-methyl-6-vinyl-pyridin-2-yl)-acetamide (compound F5) are dissolved in a mixture of each 200 ml methanol and dichloromethane and cooled to −80° C. Subsequently, ozone is passed into the solution (flow 20-25 l/h ozone). After 5 min ozone treatment is stopped. Thereafter, nitrogen is applied for 5 min and 7.44 g of triphenylphosphane are added while stirring is continued. The solution is allowed to warm up to r.t. Subsequently, the volatile components are removed in vacuo and the residue is purified by chromatography on silica gel (eluent cyclohexane/ethyl acetate 3:1) to afford 2.72 g of the title compound as colourless solid. M.p. 202° C. GC-MS: 178.2 (M$^+$). TLC: Rf=0.50 (cyclohexane/ethyl acetate 1:1). [Remark: Occasionally remaining traces of triphenylphosphine oxide can be removed by dissolving crude product in ethyl acetate followed by cooling to precipitate triphenylphosphine oxide.]

E3. Methyl 4-methoxy-pyridin-2,6-dicarboxylic acid 3.0 g of dimethyl 4-methoxy-pyridin-2,6-dicarboxylic acid (compound F6) are dissolved in 280 ml of water and 420 ml of methanol. After cooling to 0° C., 14.65 ml of a sodium hydroxide solution (strength 1.0 M) is added dropwise (15 min). After 1 h, the mixture is allowed to warm up to room temperature and is stirred for further 21 h during which time 2.0 ml of sodium hydroxide solution are gradually added. Subsequently, 6.5 g of acidic ion exchange resin (Amberlite IR-120 [H$^+$]) are added for neutralization. Thereafter, the mixture is filtered and the filtrate is concentrated in vacuum to yield 2.8 g of the title compound as a colorless oil. TSP-MS: 212.1 [MH$^+$]. TLC: Rf=0.1-0.2 (dichlormethane/methanol 5:1, 3.0 vol.-% acetic acid).

F1. 2,3-Diamino-5-p-tolyl-pyridine

A solution of 3.25 g of 2-amino-5-(p-tolyl)-3-nitro-pyridine (compound G3) and 325 mg of Pd/C (10%) in 260 ml of methanol is treated with hydrogen under vigorous stirring at room temperature for 18 h. The suspension is filtered with suction through a celite pad. The colorless filtrate is evaporated to dryness to afford 2.63 g of the pure title compound of m.p. 141° C. MS: 200.3 (MH$^+$).

TLC: Rf=0.46 (dichloromethane/methanol 10:1).

F2. 2,3-Diamino-5-(4-fluoro-phenyl)-pyridine

A solution of 2.59 g of 2-amino-5-(4-fluorophenyl)-3-nitro-pyridine (compound G1) in 36 ml ethanol is treated with 12.9 g of SnCl$_2$.2H$_2$O at 90° C. for 24 h under a nitrogen atmosphere. Thereafter, the solution is concentrated to dryness. The residue is dissolved in 600 ml H$_2$O and adjusted to pH 8 using a 1.0 M solution of aqueous sodium hydroxide. Subsequently, the aqueous layer is extracted six times each with 50 ml of ethyl acetate. The combined organic phases are extracted once with 100 ml of brine, dried using magnesium sulfate, filtered with suction, and evaporated to dryness to yield 2.12 g of the pure title compound of m.p. 261° C. MS: 204.3 (MH$^+$). TLC: Rf=0.50 (dichloromethane/methanol 5:1).

F3. 2,3-Diamino-5-(4-dimethylamino-phenyl)-pyridine

A solution of 3.30 g of 2-amino-5-(4-dimethylaminophenyl)-3-nitro-pyridine (compound G2) and 330 mg of Pd/C (10%) in 260 ml of methanol is treated with hydrogen under vigorous stirring at room temperature for 17 h. The suspension is filtered with suction through a celite pad. The colorless filtrate is evaporated to dryness to afford 2.85 g of the pure title compound of m.p. 155° C. MS: 229.3 (MH$^+$). TLC: Rf=0.38 (dichloromethane/methanol 10:1).

F4. 2,3-Diamino-5-(4-chlorophenyl)-pyridine

A solution of 1.19 g of 2-amino-5-(4-chlorophenyl)-3-nitro-pyridine in 17 ml of ethanol is treated with 5.5 g of SnCl$_2$.2H$_2$O at 90° C. for 17 h under a nitrogen atmosphere. Thereafter, the solution is concentrated in vacuo to dryness. The residue is dissolved in 300 ml of water and adjusted to pH 8 using a 1.0 M solution of aqueous sodium hydroxide. Subsequently, the aqueous layer is extracted four times each with 50 ml of ethyl acetate. The combined organic phases are extracted once with 50 ml of brine, dried using MgSO$_4$, filtered with suction, and evaporated to dryness to yield 1.05 g of the pure title compound of m.p. 178° C. MS: 220.3 (MH$^+$). MS: 220.3/222.3 (MH$^+$, 100%/20%). TLC: Rf=0.30 (dichloromethane/methanol 5:1).

F5. N-(4-Methyl-6-vinyl-pyridin-2-yl)-acetamide 37.5 g of N-(6-bromo-4-methyl-pyridin-2-yl)-acetamide (compound G4) is dissolved in 750 ml anoxic dioxane under a nitrogen atmosphere. Subsequently, 70.3 ml of vinyl tributylstannane and 11.5 g trans-dichloro-bis(triphenylphosphane)palladium-(II) are added. The reaction mixture is heated to 100° C. for 65 h. Thereafter, the volatile components are removed in vacuo and the remaining residue is purified by chromatography on silica gel (eluent: toluene/ethyl acetate 6:1) to afford 21.0 g of the title compound. M.p. 140° C. GC-MS: 176.2 (M$^+$). TLC: Rf=0.40 (toluene/ethyl acetate 4:1).

F6. Dimethyl 4-methoxy-pyridin-2,6-dicarboxylic acid

The title compound is synthesized from commercially available chelidamic acid in two steps according to J. B.

Lamture, T. G. Wensel, Tetrahedron Lett. 1993, 34(26), 4141-4144 and J. J. Parlow, J. Heterocycl. Chem. 1998, 35(6), 1493-1500.

G1. 2-Amino-5-(4-fluoro-phenyl)-3-nitro-pyridine 5.0 g of 2-amino-5-bromo-3-nitropyridine are dissolved in 120 ml of anoxic dioxane under a nitrogen atmosphere. Subsequently, 69 ml of an aqueous sodium bicarbonate solution (2.0 M), 5.4 g of 4-fluorophenyl-boronic acid, and 1.0 g of trans-dichloro-bis(tricyclohexylphosphane)palladium-(II) are added. The reaction mixture is refluxed at 110° C. for 17 hours. Thereafter, the volatile components are removed in vacuo and the remaining residue is redissolved in 2.0 l of a mixture of water/dichloromethane (1:1). The aqueous phase is extracted four times each with 625 ml of dichloromethane. The organic layer is separated, dried using sodium sulfate, and evaporated to dryness to yield a colorless, crude solid. Subsequently, the residue is purified by flash chromatography on silica gel (eluent: toluene/ethyl acetate 20:1) to afford 5.35 g of the title compound as a colorless solid of m.p. 232° C. MS: 234.2 (MH$^+$). TLC: Rf=0.30 (toluene/ethyl acetate 20:1).

G2. 2-Amino-5-(4-dimethylamino-phenyl)-3-nitro-pyridine 4.36 g of 2-amino-5-bromo-3-nitropyridine are dissolved in 73 ml of anoxic dioxane under a nitrogen atmosphere. Subsequently, 60 ml of an aqueous sodium bicarbonate solution (2.0 M), 7.3 g of 4-dimethylaminophenyl-boronic acid, and 0.886 g of trans-dichloro-bis(tricyclohexylphosphane)palladium-(II) are added. The reaction mixture is refluxed at 110° C. for 19 hours. Thereafter, the volatile components are removed in vacuo and the remaining residue is redissolved in 1.0 l of a mixture of water/dichloromethane (1:1). The aqueous phase is extracted four times each with 500 ml of dichloromethane. The organic layer is separated, dried using sodium sulfate, and evaporated to dryness to yield a colorless, crude solid. Subsequently, the residue is purified by flash chromatography on silica gel (eluent: dichloromethane/ethanol 50:1) to afford 3.41 g of the title compound as a colorless solid of m.p. 212° C. MS: 259.2 (MH$^+$). TLC: Rf=0.55 (dichloromethane/ethanol 50:1).

G3. 2-Amino-5-(4-p-tolyl)-3-nitro-pyridine

Compound G3 can be prepared analogously as described in Example G1 and G2.

G4. N-(6-Bromo-4-methyl-pyridin-2-yl)-acetamide

Peracetylation of the mixture containing N-(6-bromo-4-methyl-pyridin-2-yl)-acetamide and 2-amino-6-bromo-4-methyl-pyridine (compound H1) can be performed by a person skilled in the art according to Einhorn's procedure, thereby using pyridine, acetic anhydride, and N,N-dimethylamino-pyridine. The pure title compound is obtained as a colourless, amorphous solid in up to 89% yield after chromatography on silica gel (eluent: toluene/ethyl acetate 4:1). M.p. 190° C. TSP-MS: 228.9/230.8 (MH$^+$; 92%, 100%).

TLC: Rf=0.50 (toluene/ethyl acetate 4:1).

H1. N-(6-Bromo-4-methyl-pyridin-2-yl)-acetamide/ 2-Amino-6-bromo-4-methyl-pyridine A mixture of the title compounds can be obtained by cyclization of 3-hydroxy-3-methyl-pentanedinitrile (compound I1) in the presence of HBr in glacial acetic acid according to the procedure as described in F. Johnson et al., *J. Org. Chem.* 1962, 27, 2473-2478.

(Remark: The more water commercially available HBr in glacial acetic acid contains, the less N-(6-bromo-4-methyl-pyridin-2-yl)-acetamide and the more 2-amino-6-bromo-4-methyl-pyridine are produced.)

I1. 3-Hydroxy-3-methyl-pentanedinitrile

The title compound can be prepared from 2-chloromethyl-2-methyl-oxirane and potassium cyanide as described in EP 052093, the disclosure of which is incorporated herein.

COMMERCIAL APPLICABILITY

The compounds according to the invention have valuable pharmacological properties which make them commercially utilizable. They are selective inhibitors of the enzyme inducible nitric oxide synthase. Nitric oxide synthases (NO-synthases, NOSs) are enzymes that generate NO and citrulline from the amino acid arginine. In certain pathophysiological situations such as arginine depletion or tetrahydrobiopterin depletion the generation of $O_2$. from NO-synthases instead or together with NO has been reported. NO is long known as a signalling molecule in most living organisms including mammals and humans. The most prominent action of NO is it's smooth muscle relaxing activity, which is caused on the molecular level by the activation of soluble guanylate cyclase. In the last years a lot of other enzymes have been shown to be regulated by NO or reaction products of NO.

There exist three isoforms of NO-synthases which fall into two classes and differ in their physiologic functions and molecular properties. The first class, known as constitutive NO-synthases, comprises of the endothelial NO-synthase and the neuronal NO-synthase. Both isoenzymes are expressed constitutively in various cell types, but are most prominent in endothelial cells of blood vessel walls (therefore called endothelial NO-synthase, eNOS or NOS-III) and in neuronal cells (therefore called neuronal NO-synthase, nNOS or NOS-I). Activation of these two enzymes is dependent on $Ca^{2+}$/Calmodulin which is generated by transient increases of the intracellular free $Ca^{2+}$ concentration. Activation of constitutive isoforms leads to transient bursts of nitric oxide resulting in nanomolar cellular or tissue NO concentrations. The endothelial isoform is involved in the physiologic regulation of blood pressure. NO generated by the neuronal isoform seems to have neurotransmitter function and the neuronal isoform is among other regulatory processes involved in memory function (long term potentiation).

In contrast to the constitutive isoforms the activation of inducible NO-synthase (iNOS, NOS-II), the sole member of the second class, is performed by transcriptional activation of the iNOS-promoter. Proinflammatory stimuli lead to transcription of the gene for inducible NO-synthase, which is catalytically active without increases in the intracellular $Ca^{2+}$-concentration. Due to the long half live of the inducible NO-synthase and the unregulated activity of the enzyme, high micromolar concentrations of NO are generated over longer time periods. These high NO-concentrations alone or in cooperation with other reactive radicals such as $O_2$. are cytotoxic. Therefore, in situations of microbial infections, iNOS is involved in cell killing by macrophages and other immune cells during early nonspecific immune responses.

There are a number of pathophysiological situations which among others are characterized by the high expression of inducible NO-synthase and concomitant high NO or $O_2$. concentrations. It has been shown that these high NO concentrations alone or in combination with other radical species lead to tissue and organ damage and are causally involved in these pathophysiologies. As inflammation is characterized by the expression of proinflammatory enzymes, including inducible NO-synthase, acute and chronical inflammatory processes are promising diseases for the therapeutic application of selective inhibitors of inducible NO-synthase. Other pathophysiologies with high NO-production from inducible NO-synthase are several forms of shock (septic, hemorrhagic and cytokine-induced).

It is clear that nonselective NO-synthase inhibitors will lead to cardiovascular and neuronal side effects due to concomitant inhibition of constitutive NO-synthase isoforms.

It has been shown in in-vivo animal models of septic shock that reduction of circulating plasma NO-levels by NO-scavenger or inhibition of inducible NO-synthase restores systemic blood pressure, reduces organ damage and increases survival (deAngelo Exp. Opin. Pharmacother. 19-29, 1999; Redl et al. Shock 8, Suppl. 51, 1997; Strand et al. Crit. Care Med. 26, 1490-1499, 1998). It has also been shown that increased NO production during septic shock contributes to cardiac depression and myocardial dysfunction (Sun et al. J. Mol. Cell Cardiol. 30, 989-997, 1998). Furthermore there are also reports showing reduced infarct size after occlusion of the left anterior coronary artery in the presence of NO-synthase inhibitors (Wang et al. Am. J. Hyperttens. 12, 174-182, 1999). Considerable inducible NO-synthase activity is found in human cardiomyopathy and myocarditis, supporting the hypothesis that NO accounts at least in part for the dilatation and impaired contractility in these pathophysiologies (de Belder et al. Br. Heart. J. 4, 426-430, 1995).

In animal models of acute or chronic inflammation, blockade of inducible NO-synthase by isoform-selective or nonselective inhibitors or genetic knock out improves therapeutic outcome. It is reported that experimental arthritis (Connor et al. Eur. J. Pharmacol. 273, 15-24, 1995) and osteoarthritis (Pelletier et al. Arthritis & Rheum. 41, 1275-1286, 1998), experimental inflammations of the gastro-intestinal tract (Zingarelli et al. Gut 45, 199-209, 1999), experimental glomerulonephritis (Narita et al. Lab. Invest. 72, 17-24, 1995), experimental diabetes (Corbett et al. PNAS 90, 8992-8995, 1993), LPS-induced experimental lung injury is reduced by inhibition of inducible NO-synthase or in iNOS-knock out mice (Kristof et al. Am. J. Crit. Care. Med. 158, 1883-1889, 1998). A pathophysiological role of inducible NO-synthase derived NO or $O_2$. is also discussed in chronic inflammatory diseases such as asthma, bronchitis and COPD.

Furthermore, in models of neurodegenerative diseases of the CNS such as MPTP-induced parkinsonism, amyloid peptide induced Alzheimer's disease (Ishii et al., FASEB J. 14, 1485-1489, 2000), malonate induced Huntington's disease (Connop et al. Neuropharmacol. 35, 459-465, 1996), experimental meningitis (Korytko & Boje Neuropharmacol. 35, 231-237, 1996) and experimental encephalitis (Parkinson et al. J. Mol. Med. 75, 174-186, 1997) a causal participation of NO and inducible NO-synthase has been shown.

Increased iNOS expression has been found in the brains of AIDS victims and it is reasonable to assume a role of iNOS in AIDS related dementia (Bagasra et al. J. Neurovirol. 3 153-167, 1997).

Other studies implicated nitric oxide as a potential mediator of microglia dependent primary demyelination, a hallmark of multiple sclerosis (Parkinson et al. J. Mol. Med. 75, 174-186, 1997).

An inflammatory reaction with concomitant expression of inducible NO-synthase also takes place during cerebral ischemia and reperfusion (Iadecola et al. Stroke 27, 1373-1380, 1996). Resulting NO together with $O_2$. from infiltrating neutrophils is thought to be responsible for cellular and organ damage. Also, in models of traumatic brain injury (Mesenge et al. J. Neurotrauma 13, 209-214, 1996; Wada et al. Neurosurgery 43, 1427-1436, 1998) NO-synthase inhibitors have been show to possess protective properties. A regulatory role for inducible NO-synthase has been reported in various tumor cell lines (Tozer & Everett Clin Oncol. 9. 357-264, 1997).

On account of their inducible NO-synthase-inhibiting properties, the compounds according to the invention can be employed in human and veterinary medicine and therapeutics, where an excess of NO or $O_2$. due to increases in the activity of inducible NO-synthase is involved. They can be used without limitation for the treatment and prophylaxis of the following diseases:

Acute inflammatory diseases: Septic shock, sepsis, SIRS, hemorrhagic shock, shock states induced by cytokine therapy (IL-2, TNF), organ transplantation and transplant rejection, head trauma, acute lung injury, ARDS, inflammatory skin conditions such as sunburn, inflammatory eye conditions such as uveitis, glaucoma and conjunctivitis.

Chronic inflammatory diseases of peripheral organs and the CNS: gastrointestinal inflammatory diseases such as Crohn's disease, inflammatory bowel disease, ulcerative colitis, lung inflammatory diseases such as asthma and COPD, arthritic disorders such as rheumatoid arthritis, osteoarthritis and gouty arthritis, heart disorders such as cardiomyopathy and myocarditis, artherosklerosis, neurogenic inflammation, skin diseases such as psoriasis, dermatitis and eczema, diabetes, glomerulonephritis; dementias such as dementias of the Alzheimer's type, vascular dementia, dementia due to a general medical condition, such as AIDS-, Parkinson's disease, Huntington's induced dementias, ALS, multiple sclerosis; necrotizing vasculitides such as polyarteritis nodosa, serum sickness, Wegener's granulomatosis, Kawasaki's syndrome; headaches such as migraine, chronic tension headaches, cluster and vascular headaches, post-traumatic stress disorders; pain disorders such as neuropathic pain; myocardial and cerebral ischemia/reperfusion injury.

The compounds may also be useful in the treatment of cancers that express nitric oxide synthase.

The invention further relates to a method for the treatment of mammals, including humans, which are suffering from one of the abovementioned illnesses. The method is characterized in that a therapeutically active and pharmacologically effective and tolerable amount of one or more of the compounds according to the invention is administered to the ill mammal.

The invention further relates to the compounds according to the invention for use in the treatment and/or prophylaxis of illnesses, especially the illnesses mentioned.

The invention also relates to the use of the compounds according to the invention for the production of pharmaceutical compositions which are employed for the treatment and/or prophylaxis of the illnesses mentioned.

The invention also relates to the use of the compounds according to the invention for the production of pharmaceutical compositions having an iNOS inhibitory activity.

The invention furthermore relates to pharmaceutical compositions for the treatment and/or prophylaxis of the illnesses mentioned, which contain one or more of the compounds according to the invention.

The invention moreover relates to pharmaceutical compositions according to this invention having an iNOS inhibitory activity.

The pharmaceutical compositions are prepared by processes which are known per se and familiar to the person skilled in the art. As pharmaceutical compositions, the compounds according to the invention (=active compounds) are either employed as such, or preferably in combination with suitable pharmaceutical auxiliaries and/or excipients, e.g. in the form of tablets, coated tablets, capsules, caplets, suppositories, patches (e.g. as TTS), emulsions, suspensions, gels or solutions, the active compound content advantageously being between 0.1 and 95% and where, by the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with auxiliaries or excipients which are suitable for the desired pharmaceutical formulations on account of his/her expert knowledge. In addition to solvents, gel formers, ointment bases and other active compound excipients, for example antioxidants, dispersants, emulsifiers, preservatives, solubilizers, colorants, complexing agents or permeation promoters, can be used.

The administration of the pharmaceutical compositions according to the invention may be performed in any of the generally accepted modes of administration available in the art. Illustrative examples of suitable modes of administration include intravenous, oral, nasal, parenteral, topical, transdermal and rectal delivery. Oral and intravenous delivery are preferred.

For the treatment of disorders of the respiratory tract, the compounds according to the invention are preferably also administered by inhalation in the form of an aerosol; the aerosol particles of solid, liquid or mixed composition preferably having a diameter of 0.5 to 10 µm, advantageously of 2 to 6 µm.

Aerosol generation can be carried out, for example, by pressure-driven jet atomizers or ultrasonic atomizers, but advantageously by propellant-driven metered aerosols or propellant-free administration of micronized active compounds from inhalation capsules.

Depending on the inhaler system used, in addition to the active compounds the administration forms additionally contain the required excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of apparatuses are available with which aerosols of optimum particle size can be generated and administered, using an inhalation technique which is as right as possible for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhaler described in European Patent Application EP 0 505 321), using which an optimal administration of active compound can be achieved.

For the treatment of dermatoses, the compounds according to the invention are in particular administered in the form of those pharmaceutical compositions which are suitable for topical application. For the production of the pharmaceutical compositions, the compounds according to the invention (=active compounds) are preferably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, pastes, gels or solutions.

The pharmaceutical compositions according to the invention are prepared by processes known per se. The dosage of the active compounds is carried out in the order of magnitude customary for iNOS inhibitors. Topical application forms (such as ointments) for the treatment of dermatoses thus contain the active compounds in a concentration of, for example, 0.1-99%. The dose for administration by inhalation is customarily between 0.1 and 10 mg per day. The customary dose in the case of systemic therapy (p.o.) is between 0.3 and 30 mg/kg per day, (i. v.) is between 0.3 and 30 mg/kg/h.

Biological Investigations

Measurement of Inducible NO-Synthase Activity

The assay is performed in 96-well microtiter F-plates (Greiner, Frickenhausen, FRG) in a total volume of 100 µl in the presence of 100 nM calmodulin, 226 µM $CaCl_2$, 477 µM $MgCl_2$, 5 µM flavin-adenine-dinucleotide (FAD), 5 µM flavin mononucleotide (FMN), 0.1 mM NADPH, 7 mM glutathione, 10 µM BH4 and 100 mM HEPES pH 7.2. Arginine concentrations are 0.1 µM for enzyme inhibition experiments. 150000 dpm of [$^3$H]arginine are added to the assay mixture. Enzyme reaction is started by the addition of 4 µg of a crude cytosolic fraction containing human inducible NO-synthase and the reaction mixture is incubated for 45 to 60 min at 37° C. Enzyme reaction is stopped by adding 10 µl of 2M MES-buffer pH 5.0. 50 µl of the incubation mixture is transferred into a MADP N65 filtration microtiter plate (Millipore, Eschborn, FRG) containing already 50 µl of AG-50W-X8 cation exchange resin (Biorad, München, FRG). The resin in the Na loaded form is pre-equilibrated in water and 70 µl (corresponding to 50 µl dry beads) are pipetted under heavy stirring with a 8 channel pipette into the filtration plate. After pipetting 50 µl of the enzyme reaction mixture onto the filtration plates, the plates are placed on a filtration manifold (Porvair, Shepperton, UK) and the flow through is collected in Pico scintillation plates (Packard, Meriden, Conn.). The resin in the filtration plates is washed with 75 µl of water (1×50 µl and 1×25 µl) which is also collected in the same plate as the sample. The total flow through of 125 µl is mixed with 175 µl of Microscint-40 scintillation cocktail (Packard) and the scintillation plate is sealed with TopSeal P-foil (Packard). Scintillation plates are counted in a scintillation counter.

For the measurement of inducible NO-synthase-inhibiting potencies of compounds increasing concentrations of inhibitors were included into the incubation mixture. $IC_{50}$-values were calculated from the percent inhibition at given concentrations by nonlinear least square fitting.

Representative inhibitory values determined for the compounds according to the invention follow from the following table A, in which the compound numbers correspond to the example numbers.

TABLE A

Inhibition of INOS activity [measured as $-\log IC_{50}$ (mol/l)]

| compound | $-\log IC_{50}$ |
|---|---|
| 1 | The inhibitory |
| 2 | values of these |
| 4 | mentioned |
| 5 | Examples lie in |
| 6 | the range from |
| 7 | 6.58 to 8.15 |
| 8 | |
| 9 | |
| 10 | |
| 11 | |
| 12 | |
| 14 | |
| 15 | |
| 16 | |
| 17 | |

TABLE A-continued

Inhibition of INOS activity [measured as $-\log IC_{50}$ (mol/l)]

| compound | $-\log IC_{50}$ |
|---|---|
| 18 | |
| 19 | |
| 20 | |
| 21 | |
| 22 | |

The invention claimed is:

1. A method for inhibiting iNOS activity in a patient comprising administering to said patient a therapeutically effective amount of a compound of formula I

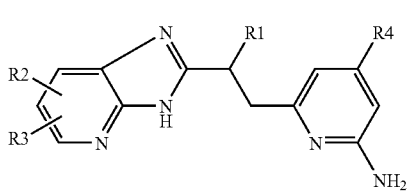

(I)

in which
R1 is hydrogen or 1-4C-alkyl,
R2 is hydrogen, halogen, hydroxyl, nitro, amino, 1-7C-alkyl, trifluoromethyl, 3-7C-cycloalkyl, 3-7C-cycloalky-1-1-4C-alkyl, 1-4C-alkoxy, completely or predominantly fluorine-substituted 1-4C-alkoxy, 1-4C-alkoxy-1-4C-alkyl, 1-4C-alkoxy-1-4C-alkoxy, 1-4C-alkoxycarbonyl, mono- or di-1-4C-alkylaminocarbonyl, mono- or di-1-4C-alkylaminosulfonyl, 1-4C-alkylcarbonylamino, 1-4C-alkylsulfonylamino, phenyl, R21- and/or R211-substituted phenyl, phenyl-1-4C-alkyl, phenyl-1-4C-alkyl wherein the phenyl moiety is substituted by R22, phenyl-1-4C-alkoxy, pyridyl, pyridyl substituted by
R23, pyridyl-1-4C-alkyl, or pyridyl-1-4C-alkyl wherein the pyridyl moiety is substituted by R24, in which
R21 is cyano, halogen, carboxyl, 1-4C-alkyl, 1-4C-alkoxy, aminocarbonyl, mono- or di-1-4C-alkylaminocarbonyl, 1-4C-alkylcarbonylamino, 1-4C-alkoxycarbonyl, aminosulfonyl, mono- or di-1-4C-alkylaminosulfonyl, amino, mono- or di-1-4C-alkylamino, trifluoromethyl, hydroxyl, phenylsulfonylamino, phenyl-1-4C-alkoxy, or —S(O)$_2$-Het, in which
Het is bonded to the adjacent sulfonyl group via a ring nitrogen atom, and is a 3- to 7-membered fully saturated heterocyclic ring comprising one nitrogen atom, to which the sulfonyl group is attached, and optionally one further heteroatom selected from the group consisting of N(R210), oxygen and sulfur, in which
R210 is 1-4C-alkyl,
R211 is halogen or 1-4C-alkoxy,
R22 is halogen, 1-4C-alkyl or 1-4C-alkoxy,
R23 is halogen, 1-4C-alkyl or 1-4C-alkoxy,
R24 is halogen, 1-4C-alkyl or 1-4C-alkoxy,
R3 is hydrogen, halogen, 1-4C-alkyl or 1-4C-alkoxy,
R4 is 1-4C-alkyl, or 1-4C-alkoxy,
or a pharmaceutically acceptable salt, N-oxide or salt of an N-oxide thereof.

2. The method according to claim 1, in which
R1 is hydrogen or 1-2C-alkyl,
R2 is hydrogen, halogen, phenyl, or R21- and/or R211-substituted phenyl, in which
R21 is 1-4C-alkyl, cyano, halogen, mono- or di-1-4C-alkylamino, trifluoromethyl, mono-or di-1-4C-alkylaminosulfonyl, hydroxyl, phenyl-1-4C-alkoxy, or —S(0)$_2$-Het, in which Het is azetidin-1-yl, pyrrolidin-1-yl, piperidin-1-yl, or 4N-(R210)-piperazin-1-yl, in which
R210 is 1-4C-alkyl,
R211 is halogen,
R3 is hydrogen,
R4 is methyl, or methoxy,
or a pharmaceutically acceptable salt, N-oxide or salt of an N-oxide thereof.

3. The method according to claim 1,
in which
R1 is hydrogen, methyl or ethyl,
R2 is hydrogen, iodine, bromine, phenyl, or R21- and/or R211-substituted phenyl, in which
R21 is methyl, cyano, chlorine, fluorine, dimethylamino, trifluoromethyl, dimethylaminosulfonyl, hydroxyl, benzyloxy, or —S(O)$_2$-Het, in which
Het is azetidin-1-yl, pyrrolidin-1-yl, piperidin-1-yl, or 4N-methyl-piperazin-1-yl, in which
R211 is chlorine,
R3 is hydrogen,
R4 is methyl, or methoxy,
or a pharmaceutically acceptable salt, N-oxide or salt of an N-oxide thereof.

4. The method according to claim 1,
in which
R1 is hydrogen or methyl,
R2 is bonded in the 6-position of the 3H-imidazo[4,5-b] pyridine ring, and is hydrogen, iodine, bromine, phenyl, 3-hydroxyl-phenyl, 4-(R21)-phenyl, or 3,5-di-chloro-phenyl, in which
R21 is methyl, cyano, chlorine, fluorine, dimethylamino, trifluoromethyl, dimethylaminosulfonyl, benzyloxy, or —S(O)$_2$-Het, in which
Het is azetidin-1-yl, pyrrolidin-1-yl, piperidin-1-yl, or 4N-methyl-piperazin-1-yl, in which
R3 is hydrogen,
R4 is methyl, or methoxy,
or a pharmaceutically acceptable salt, N-oxide or salt of an N-oxide thereof.

5. The method according to claim 1,
in which
R1 is hydrogen or 1-4C-alkyl,
R2 is hydrogen, halogen, hydroxyl, nitro, amino, 1-7C-alkyl, trifluoromethyl, 3-7C-cycloalkyl, 3-7C-cycloalkyl-1-4C-alkyl, 1-4C-alkoxy, completely or predominantly fluorine-substituted 1-4C-alkoxy, 1-4C-alkoxy-1-4C-alkyl, 1-4C-alkoxy-1-4C-alkoxy, 1-4C-alkoxycarbonyl, mono- or di-1-4C-alkylaminocarbonyl, mono- or di-1-4C-alkylaminosulfonyl, 1-4C-alkylcarbonylamino, 1-4C-alkylsulfonylamino, phenyl, R21- and/or R211-substituted phenyl, phenyl-1-4C-alkyl, phenyl-1-4C-alkyl wherein the phenyl moiety is substituted by R22, phenyl-1-4C-alkoxy, pyridyl, pyridyl substituted by
R23, pyridyl-1-4C-alkyl, pyridyl-1-4C-alkyl wherein the pyridyl moiety is substituted by
R24, in which
R21 is cyano, halogen, carboxyl, 1-4C-alkyl, 1-4C-alkoxy, aminocarbonyl, mono- or di-1-4C-alkylaminocarbonyl, 1-4C-alkylcarbonylamino, 1-4C-alkoxycarbonyl, aminosulfonyl, mono- or di-1-4C-alkylaminosulfonyl, amino, mono- or di-1-4C-alkylamino, trifluoromethyl, hydroxyl, phenylsulfonylamino or phenyl-1-4C-alkoxy,
R211 is halogen or 1-4C-alkoxy,
R22 is halogen, 1-4C-alkyl or 1-4C-alkoxy,
R23 is halogen, 1-4C-alkyl or 1-4C-alkoxy,
R24 is halogen, 1-4C-alkyl or 1-4C-alkoxy, R3 is hydrogen, halogen, 1-4C-alkyl or 1-4C-alkoxy,
R4 is 1-4C-alkyl,
or a pharmaceutically acceptable salt, N-oxide or salt of an N-oxide thereof.

6. The method according to claim 1,
in which
R1 is hydrogen, methyl or ethyl,
R2 is hydrogen, iodine, bromine, phenyl, or R21-substituted phenyl, in which
R21 is methyl, cyano, chlorine, fluorine, dimethylamino or trifluoromethyl,
R3 is hydrogen,
R4 is methyl,
or a salt, N-oxide or a salt of an N-oxide thereof.

7. The method according to claim 1,
in which
R1 is hydrogen or methyl,
R2 is R21-substituted phenyl, in which
R21 is aminosulphonyl, mono- or di-1-4C-alkylaminosulfonyl, or —S(O)$_2$-Het, in which
Het is azetidin-1-yl, pyrrolidin-1-yl, piperidin-1-yl, or 4N-(1-4C-alkyl)-piperazin-1-yl,
R3 is hydrogen,
R4 is methyl, or methoxy,
or a pharmaceutically acceptable salt, N-oxide or salt of an N-oxide thereof.

8. The method according to claim 1, wherein the compound of formula I is of the formula Ia

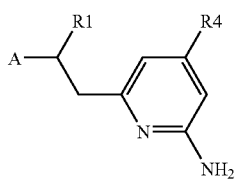

in which
R1 is hydrogen,
R4 is methyl or methoxy, and
A is 6-(4-dimethylaminosulphonyl-phenyl)-3H-imidazo[4,5-b]pyridin-2-yl, 6-(4-diethylaminosulphonyl-phenyl)-3H-imidazo[4,5-b]pyridin-2-yl, 6-(4-methylaminosulphonyl-phenyl)-3H-imidazo[4,5-b]pyridin-2-yl, 6-(4-aminosulphonyl-phenyl)-3H-imidazo[4,5-b]pyridin-2-yl, 6-(4-ethylaminosulphonyl-phenyl)-3H-imidazo[4,5-b]pyridin-2-yl, 6[4-(azetidine-1-sulfonyl)-phenyl]-3H-imidazo[4,5-b]pyridin-2-yl, 6[4-(pyrrolidine-1-sulfonyl)-phenyl]-3H-imidazo[4,5-b]pyridin-2-yl, 6-[4-(piperidine-1-sulfonyl)-phenyl]-3H-imidazo[4,5-b]pyridin-2-yl, or 6[4-(4-methyl-piperazine-1-sulfonyl)-phenyl]-3H-imidazo[4,5-b]pyridin-2-yl,
or a pharmaceutically acceptable salt, N-oxide or salt of an N-oxide thereof.

9. The method according to claim 1,
in which
R1 is hydrogen,
R2 is bonded to the 6-position of the 3H-imidazo[4,5-b]pyridine ring,
R3 is hydrogen, and
R4 is methyl;
or a pharmaceutically acceptable salt, N-oxide or salt of an N-oxide thereof.

10. The method according to claim 1, wherein the compound is selected from the group consisting of:
a. 2[2-(2-Amino-4-methylpyridin-6-yl)ethyl]-3H-imidazo[4,5-b]pyridine,
b. (R,S)-2[3-(2-Amino-4-methylpyridin-6-yl)prop-2-yl]-3H-imidazo[4,5-b]pyridine,
c. (R,S)-2[4-(2-Amino-4-methylpyridin-6-yl)but-2-yl]-3H-imidazo[4,5-b]pyridine,
d. 2[2-(2-Amino-4-methylpyridin-6-yl)ethyl]-6-bromo-3H-imidazo[4,5-b]pyridine,
e. 2[2-(2-Amino-4-methylpyridin-6-yl)ethyl]-6-phenyl-3H-imidazo[4,5-b]pyridine,
f. 2[2-(2-Amino-4-methylpyridin-6-yl)ethyl]-6-(4-cyanophenyl)-3H-imidazo[4,5-b]pyridine,
g. 2[2-(2-Amino-4-methylpyridin-6-yl)ethyl]-6-p-tolyl-3H-imidazo[4,5-b]pyridine,
h. 2-[2-(2-Amino-4-methylpyridin-6-yl)ethyl]-6-(4-fluoro-phenyl)-3H-imidazo[4,5-b]pyridine,
i. 2-[2-(2-Amino-4-methylpyridin-6-yl)ethyl]-6-(4-dimethylamino-phenyl)-3H-imidazo[4,5-b]pyridine,
j. 2[2-(2-Amino-4-methylpyridin-6-yl)ethyl]-6-(4-chlorophenyl)-3H-imidazo[4,5-b]pyridine,
k. 2[2-(2-Amino-4-methylpyridin-6-yl)ethyl]-6-(4-iodophenyl)-3H-imidazo[4,5-b]pyridine,
l. 2[2-(2-Amino-4-methylpyridin-6-yl)ethyl]-6-(4-trifluoromethyl-phenyl)-3H-imidazo[4,5-b]pyridine,
m. 6-{2[6-(3-Benzyloxy-phenyl)-3H-imidazo[4,5-b]pyridin-2-yl]ethyl}-4-methyl-pyridin-2-ylamine,
n. 6-{2[6-(3,5-Dichloro-phenyl)-3H-imidazo[4,5-b]pyridin-2-yl]-ethyl}-4-methyl-pyridin-2-ylamine,
o. 6-{2[6-(4-Benzyloxy-phenyl)-3H-imidazo[4,5-b]pyridin-2-yl]ethyl}-4-methyl-pyridin-2-ylamine,
p. 3-{2[2-(6-Amino-4-methyl-pyridin-2-yl)-ethyl]-3H-imidazo[4,5-b]pyridin-6-yl }-phenol,
q. 6-(2-{6[4-(Azetidine-1-sulfonyl)-phenyl]-3H-imidazo[4,5-b]pyridin-2-yl}-ethyl)-4-methyl-pyridin-2-ylamine,
r. 4-Methyl -6-(2-{6[4-(pyrrolidine-1-sulfonyl)-phenyl]-3H-imidazo[4,5-b]pyridin-2-yl}-ethyl)-pyridin-2-ylamine,
s. 4-Methyl -6-(2-{6[4-(piperidine-1-sulfonyl)-phenyl]-3H-imidazo[4,5-b]pyridin-2-yl}-ethyl)-pyridin-2-ylamine,
t. 4-{2[2-(6-Amino-4-methyl-pyridin-2-yl)-ethyl]-3H-imidazo[4,5-b]pyridin-6-yl}-N,N-dimethyl-benzenesulfonamide,
u. 4-Methyl-6-(2-{6-[4-(4-methyl-piperazine-1-sulfonyl)-phenyl]-3H-imidazo[4,5-b]pyridin-2-yl}ethyl)-pyridin-2-ylamine,
v. 2[2-(2-Amino-4-methoxypyridin-6-yl)ethyl]-3H-imidazo[4,5-b]pyridine
and the pharmaceutically acceptable salts, N-oxides and salts of the N-oxides thereof.

* * * * *

UNITED STATES PATENT AND TRADEMARK OFFICE
CERTIFICATE OF CORRECTION

PATENT NO. : 7,781,453 B2  Page 1 of 1
APPLICATION NO. : 11/984364
DATED : August 24, 2010
INVENTOR(S) : Thomas Fuchss It is certified that error appears in the above-identified patent and that said Letters Patent is hereby corrected as shown below:

Claim 1, Column 47, Lines 30-31:

Delete "3-7C-cycloalky-1-1-4C-alkyl,..."

and replace with

-- 3-7C-cycloalkyl-1-4C-alkyl, --

Claim 2, Column 48, Lines 3-4:

Delete "...or —S(0)$_2$-Het..."

and replace with

-- or —S(O)$_2$-Het --

Signed and Sealed this

Second Day of November, 2010

David J. Kappos
*Director of the United States Patent and Trademark Office*